US012788524B2

(12) United States Patent
Roberson et al.

(10) Patent No.: US 12,788,524 B2
(45) **Date of Patent: *Nov. 10, 2026**

(54) ULTRASONIC SURGICAL INSTRUMENT WITH TRANSDUCER LOCKING FEATURE

(71) Applicant: Cilag GmbH International, Zug (CH)

(72) Inventors: Eric Roberson, Cincinnati, OH (US); William D. Dannaher, Cincinnati, OH (US); Stephen M. Leuck, Milford, OH (US); Fajian Zhang, Mason, OH (US); Cody R. Jackson, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 669 days.

This patent is subject to a terminal disclaimer.

(21) Appl. No.: 18/320,305

(22) Filed: May 19, 2023

(65) Prior Publication Data

US 2023/0285105 A1 Sep. 14, 2023

Related U.S. Application Data

(63) Continuation of application No. 16/779,761, filed on Feb. 3, 2020, now Pat. No. 11,712,318, which is a (Continued)

(51) Int. Cl.

*A61B 18/18* (2006.01)
*A61B 17/32* (2006.01)

(Continued)

(52) U.S. Cl.

CPC ...... *A61B 90/03* (2016.02); *A61B 17/320068* (2013.01); *A61N 7/02* (2013.01);

(Continued)

(58) Field of Classification Search

CPC ........ A61B 1/00042; A61B 17/320068; A61B 2017/0046; A61B 2017/00477;

(Continued)

(56) References Cited

U.S. PATENT DOCUMENTS

| | | | |
|---|---|---|---|
| 5,322,055 A | 6/1994 | Davison et al. |
| 5,776,155 A | 7/1998 | Beaupre et al. |

(Continued)

FOREIGN PATENT DOCUMENTS

| | | |
|---|---|---|
| CN | 103027720 A | 4/2013 |
| JP | 2000-506430 A | 5/2000 |
| JP | 2013-081779 A | 5/2013 |

OTHER PUBLICATIONS

Chinese Office Action, The First Office Action, and First Search dated Sep. 5, 2022, for Application No. 201780077863.6, 8 pages.

(Continued)

*Primary Examiner* — Michael F Peffley
*Assistant Examiner* — Amanda L Zink
(74) *Attorney, Agent, or Firm* — FBT Gibbons LLP

(57) ABSTRACT

A surgical instrument includes a body, an ultrasonic transducer assembly, and a transducer lock having a lock member configured to move between unlocked and locked positions. The transducer assembly is rotatably mounted along a longitudinal axis within the body such that the transducer assembly is configured to selectively rotate about the longitudinal axis. With the lock member in the unlocked position, the transducer assembly is configured to be selectively rotated about the longitudinal axis relative to the body. With the lock member in the locked position, the transducer lock is configured to seize the transducer assembly and inhibit rotation relative to the housing for coupling with an acoustic waveguide. The surgical instrument may also include an integral torque wrench for coupling the acoustic waveguide with a predetermined torque and an integral torque indictor for signaling to a user that the acoustic waveguide is coupled with the predetermined torque.

18 Claims, 27 Drawing Sheets

Related U.S. Application Data continuation of application No. 15/378,452, filed on Dec. 14, 2016, now Pat. No. 10,646,300.

(51) Int. Cl.

| | |
|---|---|
| ***A61B 90/00*** | (2016.01) |
| ***A61N 7/02*** | (2006.01) |
| *A61B 17/00* | (2006.01) |
| *A61B 18/00* | (2006.01) |

(52) U.S. Cl.

CPC ................. *A61B 2017/0046* (2013.01); *A61B 2017/00477* (2013.01); *A61B 2017/320069* (2017.08); *A61B 2017/320071* (2017.08); *A61B 2017/320094* (2017.08); *A61B 2017/320095* (2017.08); *A61B 2018/00345* (2013.01); *A61B 2018/00601* (2013.01); *A61B 2018/00619* (2013.01); *A61B 2018/0063* (2013.01); *A61B 2090/031* (2016.02)

(58) Field of Classification Search

CPC ...... A61B 2017/2929; A61B 2017/293; A61B 2017/2946; A61B 2017/320069; A61B 2017/320071; A61B 2017/320094; A61B 2017/320095; A61B 2018/00345; A61B 2018/00601; A61B 2018/00619; A61B 2018/0063; A61B 2090/031; A61B 90/03

See application file for complete search history.

(56) References Cited

U.S. PATENT DOCUMENTS

| | | | | |
|---|---|---|---|---|
| 5,873,873 | A | 2/1999 | Smith et al. | |
| 5,893,835 | A * | 4/1999 | Witt | A61B 18/1445 606/1 |
| 5,897,523 | A | 4/1999 | Wright et al. | |
| 5,980,510 | A | 11/1999 | Tsonton et al. | |
| 5,989,264 | A | 11/1999 | Wright | |
| 6,063,098 | A | 5/2000 | Houser et al. | |
| 6,090,120 | A | 7/2000 | Wright et al. | |
| 6,325,811 | B1 | 12/2001 | Messerly | |
| 6,454,782 | B1 | 9/2002 | Schwemberger | |
| 6,589,200 | B1 | 7/2003 | Schwemberger et al. | |
| 6,752,815 | B2 | 6/2004 | Beaupre | |
| 6,773,444 | B2 | 8/2004 | Messerly | |
| 6,783,524 | B2 | 8/2004 | Anderson et al. | |
| 7,135,030 | B2 | 11/2006 | Schwemberger et al. | |
| 7,621,930 | B2 | 11/2009 | Houser | |
| 8,461,744 | B2 | 6/2013 | Wiener et al. | |
| 8,591,536 | B2 | 11/2013 | Robertson | |
| 8,623,027 | B2 | 1/2014 | Price et al. | |
| 8,986,302 | B2 | 3/2015 | Aldridge et al. | |
| 9,011,471 | B2 | 4/2015 | Timm et al. | |
| 9,023,071 | B2 | 5/2015 | Miller et al. | |
| 9,050,125 | B2 | 6/2015 | Boudreaux et al. | |
| 9,095,367 | B2 | 8/2015 | Olson et al. | |
| 9,241,732 | B2 | 1/2016 | Craig | |
| 9,381,058 | B2 | 7/2016 | Houser et al. | |
| 9,393,037 | B2 | 7/2016 | Olson et al. | |
| 9,408,622 | B2 | 8/2016 | Stulen et al. | |
| 9,539,020 | B2 | 1/2017 | Conlon et al. | |
| 9,743,946 | B2 | 8/2017 | Faller et al. | |
| 9,872,699 | B2 | 1/2018 | Boudreaux et al. | |
| 10,010,340 | B2 | 7/2018 | Hibner et al. | |
| 10,172,636 | B2 | 1/2019 | Stulen et al. | |
| 10,349,967 | B2 | 7/2019 | Hibner et al. | |
| 10,368,892 | B2 | 8/2019 | Stulen et al. | |
| 10,646,300 | B2 | 5/2020 | Roberson et al. | |
| 2006/0079874 | A1 | 4/2006 | Faller et al. | |
| 2007/0191713 | A1 | 8/2007 | Eichmann et al. | |
| 2007/0282333 | A1 | 12/2007 | Fortson et al. | |
| 2008/0200940 | A1 | 8/2008 | Eichmann et al. | |
| 2012/0116265 | A1 | 5/2012 | Houser et al. | |
| 2015/0245849 | A1 | 9/2015 | Young et al. | |
| 2015/0245850 | A1* | 9/2015 | Hibner | A61B 17/320092 606/171 |
| 2015/0265309 | A1* | 9/2015 | Boudreaux | A61B 17/320092 606/169 |
| 2016/0166275 | A1 | 6/2016 | Eichmann et al. | |
| 2020/0222142 | A1 | 7/2020 | Roberson et al. | |

OTHER PUBLICATIONS

Chinese Office Action, The First Office Action, and First Search dated Sep. 5, 2022, for Application No. 201780077862.6, 8 pages.
European Search Report and Written Opinion dated Dec. 9, 2020, for Application No. 20182916.5, 8 pages.
European Search Report and Written Opinion dated Dec. 10, 2020, for Application No. 20205500.0, 7 pages.
Indian Examination Report dated Sep. 23, 2021, for Application No. 201917020980, 9 pages.
International Search Report and Written Opinion dated Apr. 10, 2018, for International Application No. PCT/US2017/063867, 15 pages.
Japanese Office Action, Notifications of Reasons for Refusal and Search Report by Registered Search Organization dated Sep. 21, 2021, for Application No. 2019-531769, 26 pages.
Korean Office Action and Written Opinion dated Oct. 31, 2022, for Application No. 10-2019-7020377, 5 pages.
U.S. Appl. No. 61/410,603, entitled "Energy-Based Surgical Instruments," filed Nov. 5, 2010.
U.S. Appl. No. 62/176,880, entitled "Ultrasonic Surgical Device with Articulating End Effector," filed Apr. 22, 2014.

* cited by examiner

ULTRASONIC SURGICAL INSTRUMENT WITH TRANSDUCER LOCKING FEATURE

PRIORITY

This application is a continuation of U.S. patent application Ser. No. 16/779,761, entitled "Ultrasonic Surgical Instrument with Transducer Locking Feature," filed Feb. 3, 2020, published as U.S. Pub. No. 2020/0222142 on Jul. 16, 2020, and issued as U.S. Pat. No. 11,712,318 on Aug. 1, 2023, which is a continuation of U.S. patent application Ser. No. 15/378,452, entitled "Ultrasonic Surgical Instrument with Transducer Locking Feature," filed Dec. 14, 2016, and issued as U.S. Pat. No. 10,646,300 on May 12, 2020.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pat. No. 9,023,071, entitled "Ultrasonic Device for Fingertip Control," issued May 5, 2015, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," now expired, the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pat. No. 9,393,037, entitled "Surgical Instruments with Articulating Shafts," issued Jul. 19, 2016, the disclosure of which is incorporated by reference herein; U.S. Pat. No. 9,408,622, entitled "Surgical Instruments with Articulating Shafts," issued Aug. 9, 2016, the disclosure of which is incorporated by reference herein; U.S. Pat. No. 9,095,367, entitled "Flexible Harmonic Waveguides/Blades for Surgical Instruments," issued Aug. 4, 2015, the disclosure of which is incorporated by reference herein; U.S. Pat. No. 10,172,636, entitled "Articulation Features for Ultrasonic Surgical Instrument," issued Jan. 8, 2019, the disclosure of which is incorporated by reference herein; and U.S. patent application Ser. No. 14/258,179, entitled "Ultrasonic Surgical Device with Articulating End Effector," filed Apr.

22, 2014, converted to U.S. Pat. App. No. 62/176,880, now expired, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
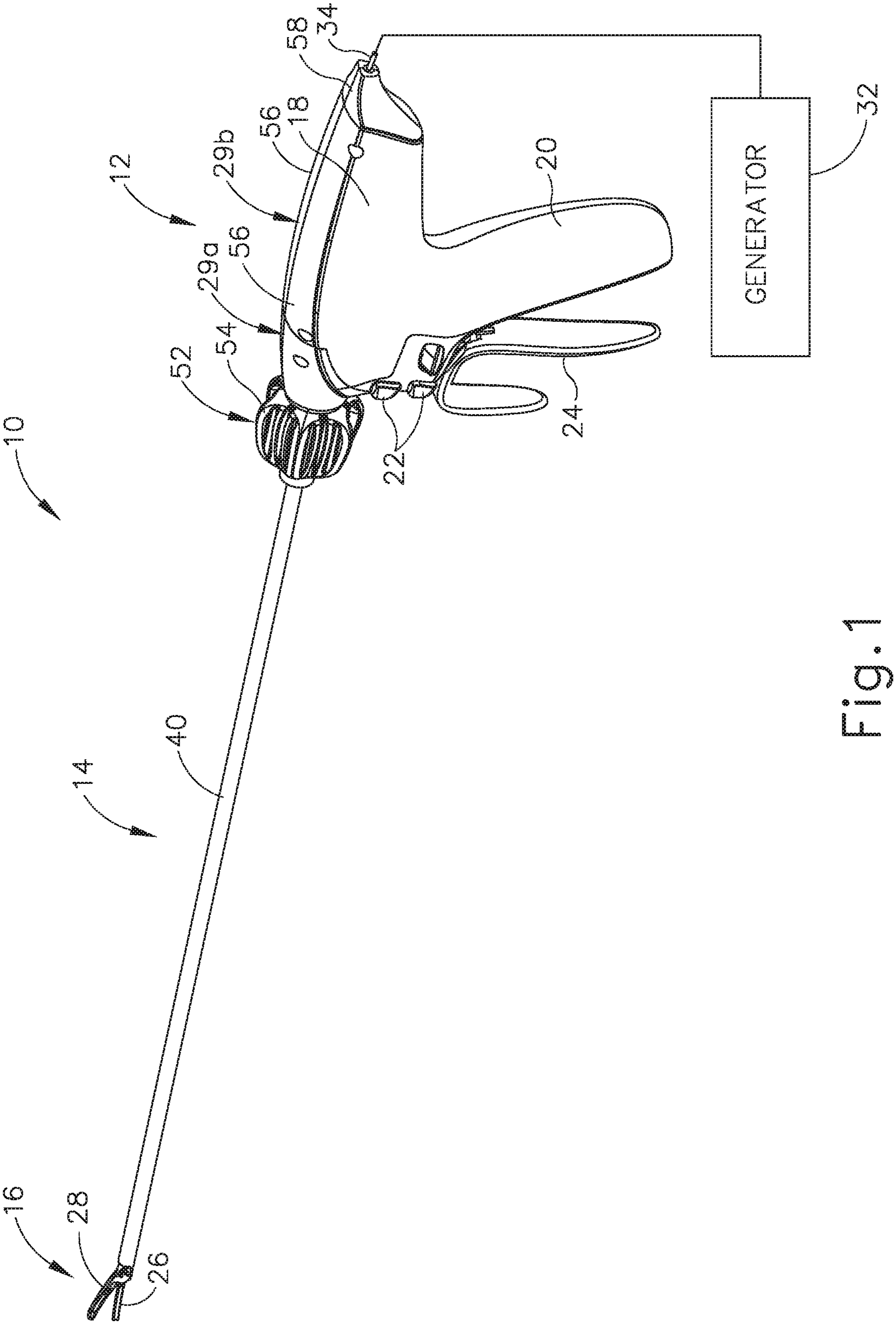
FIG. 1 depicts a perspective view of a first exemplary ultrasonic surgical instrument having a handle assembly, a shaft assembly, and an end effector.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that for convenience and clarity, spatial terms such as "upper," "lower," "inner," and "outer" are used herein with respect to the drawings. However, surgical instruments are used in many orientations and positions, and these terms are not intended to be limiting and absolute. The terms "proximal," "distal," "upper," "lower," "inner," and "outer" are thus relative terms and not intended to unnecessarily limit the invention described herein.

I. EXEMPLARY ULTRASONIC SURGICAL INSTRUMENT

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously.

Instrument (10) of the present example comprises a handle assembly (12), a shaft assembly (14), and an end effector (16). Handle assembly (12) comprises a body (18) including a pistol grip (20) and a pair of buttons (22). Handle assembly (12) also includes a trigger (24) that is pivotable toward and away from pistol grip (20). It should be understood, however, that various other suitable configurations may be used, including but not limited to a scissor grip configuration. End effector (16) includes an ultrasonic blade (26) and a pivoting clamp arm (28). Clamp arm (28) is coupled with trigger (24) such that clamp arm (28) is pivotable toward ultrasonic blade (26) in response to pivoting of trigger (24) toward pistol grip (20); and such that clamp arm (28) is pivotable away from ultrasonic blade (26) in response to pivoting of trigger (24) away from pistol grip (20). Various suitable ways in which clamp arm (28) may be coupled with trigger (24) will be apparent to those of ordinary skill in the art in view of the teachings herein. In some versions, one or more resilient members are used to bias clamp arm (28) and/or trigger (24) to the open position shown in FIG. 1.

Figure 2:
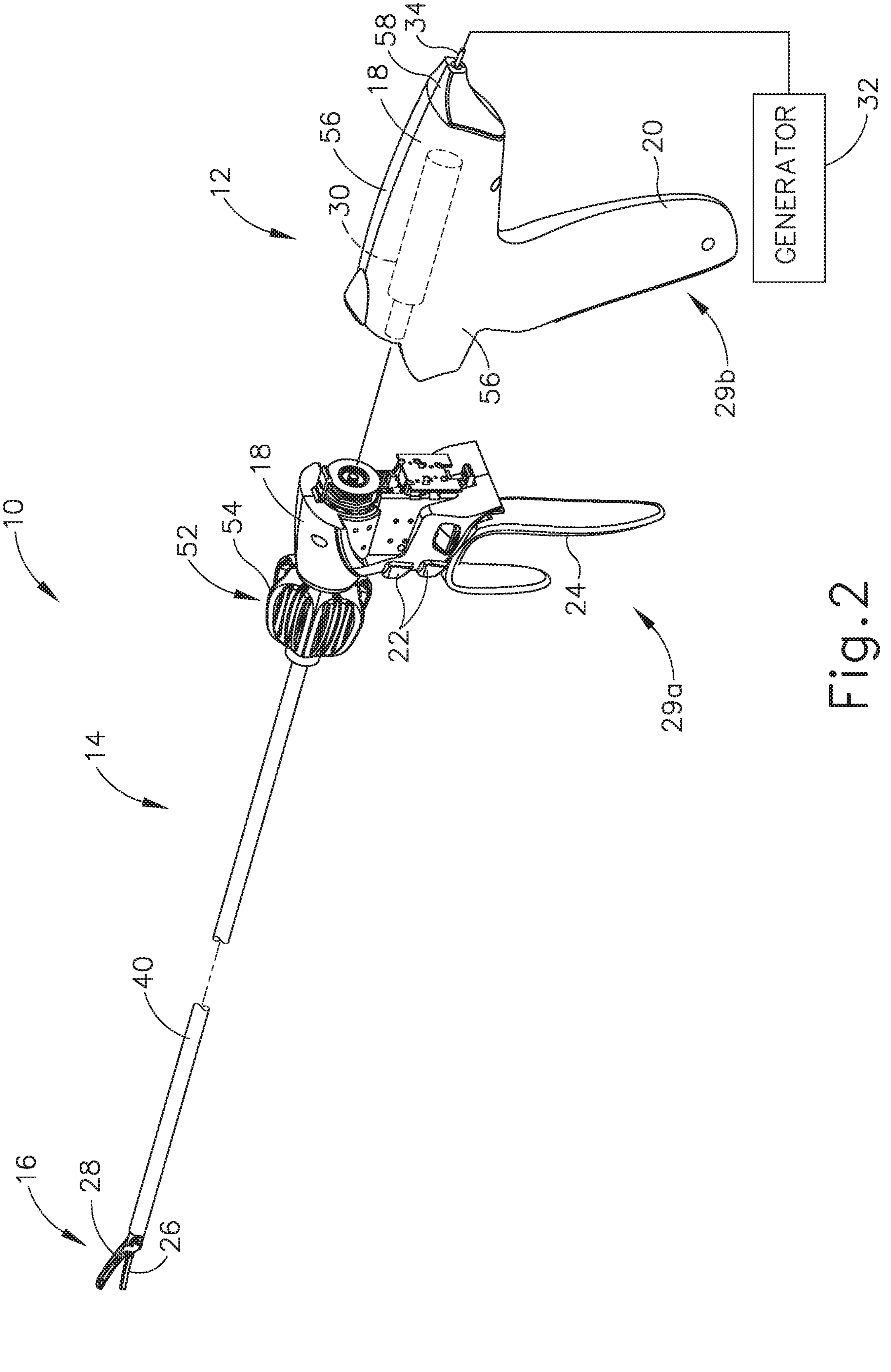
FIG. 2 depicts a partially exploded view the ultrasonic surgical instrument of FIG. 1 with a disposable portion of the ultrasonic surgical instrument removed from a reusable portion of the ultrasonic surgical instrument.

Furthermore, instrument (10) of this example comprises a disposable assembly (29*a*) and a reusable assembly (29*b*) as illustrated in FIG. 2 in more detail. By way of example, disposable assembly (29*a*) generally includes shaft assembly (14), end effector (16), buttons (22), trigger (24) and a portion of body (18). By way of further example, reusable assembly (29*b*) generally includes the remaining portion of body (18) with pistol grip (20) and an ultrasonic transducer assembly (30) (see FIG. 6A). The distal portion of reusable assembly (29*b*) is configured to removably receive the proximal portion of disposable assembly (29*a*), as seen in FIGS. 1-2, to form instrument (10). To accommodate such disposable and reusable assemblies (29*a*, 29*b*), shaft assembly (14) and ultrasonic transducer assembly (30) (see FIG. 6A) are configured to removably couple together as will be discussed below in greater detail.

Ultrasonic transducer assembly (30) is positioned within body (18) of handle assembly (12). Transducer assembly (30) is coupled with a generator (32) via a cable (34), such that transducer assembly (30) receives electrical power from generator (32) via cable (34). Piezoelectric elements in transducer assembly (30) convert electrical power from generator (32) into ultrasonic vibrations. Generator (32) may include a power source and control module that is configured to provide a power profile to transducer assembly (30) that is particularly suited for the generation of ultrasonic vibrations through transducer assembly (30). By way of example only, generator (32) may comprise a GEN04 or GEN11 sold by Ethicon Endo-Surgery, Inc. of Cincinnati, Ohio. In addition, or in the alternative, generator (32) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (32) may be integrated into handle assembly (12), and that handle assembly (12) may even include a battery or other on-board power source such that cable (34) is omitted, while other cables may alternatively be used for electrically coupling various components. Still other suitable forms that generator (32) may take, as well as various features and operabilities that generator (32) may provide, will be apparent to those of ordinary skill in the art in view of the teachings herein.

In an exemplary use, assemblies (29*a*, 29*b*) are coupled together to form instrument (10) and then is used to perform the surgical procedure. Assemblies (29*a*, 29*b*) are then decoupled from each other for further processing. In some instances, after the surgical procedure is complete, disposable assembly (29*a*) is immediately disposed of while reusable assembly (29*b*) is sterilized and otherwise processed for re-use. By way of example only, reusable assembly (29*b*) may be sterilized in a conventional relatively low temperature, relatively low pressure, hydrogen peroxide sterilization process. Alternatively, reusable assembly (29*b*) may be sterilized using any other suitable systems and techniques. In some versions, reusable assembly (29*b*) may be sterilized and reused approximately 100 times. Alternatively, reusable assembly (29*b*) may be subject to any other suitable life cycle. For instance, reusable assembly (29*b*) may be disposed of after a single use, if desired. While disposable assembly (29*a*) is referred to herein as being "disposable," it should be understood that, in some instances, disposable assembly (29*a*) may also be sterilized and otherwise processed for re-use. By way of example only, disposable assembly (29*a*) may be sterilized and reused approximately 2-30 times, using any suitable systems and techniques. Alternatively, disposable assembly (29*a*) may be subject to any other suitable life cycle.

In some versions, disposable assembly (29*a*) and/or reusable assembly (29*b*) includes one or more features that are operable to track usage of the corresponding assembly (29*a*, 29*b*), and selectively restrict operability of the corresponding assembly (29*a*, 29*b*) based on use. For instance, disposable assembly (29*a*) and/or reusable assembly (29*b*) may include one or more counting sensors and a control logic (e.g., microprocessor, etc.) that is in communication with the counting sensor(s). The counting sensor(s) may be able to detect the number of times instrument (10) is activated, the number of surgical procedures the corresponding assembly (29*a*, 29*b*) is used in, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (29*a*, 29*b*). In instances where the control logic stores two or more threshold values (e.g., a first threshold for number of activations and a second threshold for number of surgical procedures, etc.), the control logic may disable operability of one or more components in the corresponding assembly (29*a*, 29*b*) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10). Additional and/or alternative features with respect to alternative disposable and reusable assemblies (29*a*, 29*b*) may be constructed in accordance with at least some of the teachings of U.S. Pat. No. 10,349,967, entitled "Ultrasonic Surgical Instrument with Removable Handle Assembly," issued Jul. 16, 2019, the disclosure of which is incorporated by reference herein. In any case the invention described herein is not intended to be limited to use with only replaceable or reusable components as described herein.

A. Exemplary End Effector and Shaft Assembly

Figure 3A:
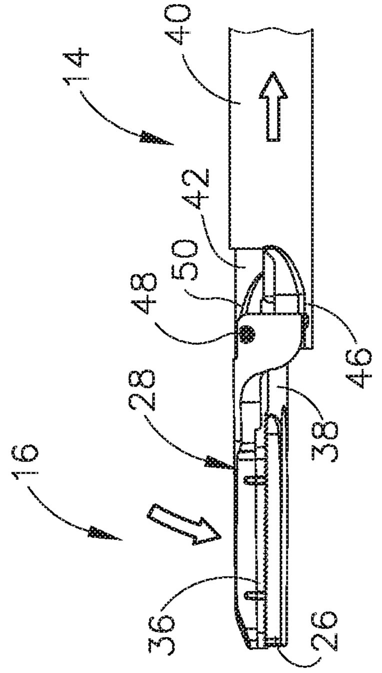
FIG. 3A depicts an enlarged side elevational view of the end effector of FIG. 1 in a closed position.
Figure 3B:
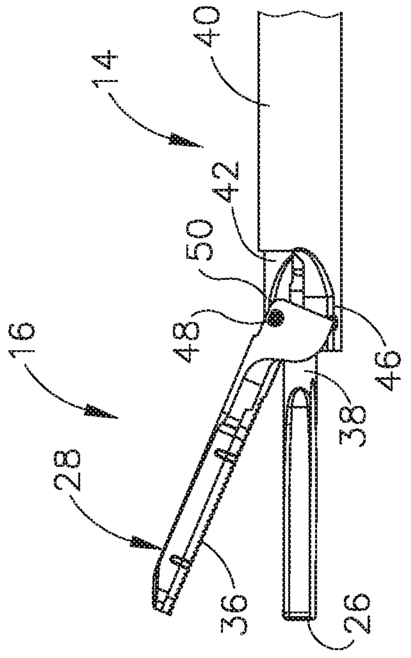
FIG. 3B depicts an enlarged side elevational view of the end effector of FIG. 1 in an open position.

As best seen in FIGS. 3A-3B, end effector (16) of this example comprises clamp arm (28) and ultrasonic blade (26) as discussed briefly above. Clamp arm (28) includes a clamp pad (36), which faces blade (26). Clamp arm (28) is pivotable toward and away from blade (26) to selectively compress tissue between clamp pad (36) and blade (26). More particularly, blade (26) is an integral feature of a distal end of an acoustic waveguide (38), which extends coaxially through tubes (40, 42), and which is configured to communicate ultrasonic vibrations to blade (26) as will be described in greater detail below.

Shaft assembly (14) comprises an outer tube (40) and an inner tube (42). Outer tube (40) is operable to translate longitudinally relative to inner tube (42) to selectively pivot clamp arm (28) toward and away from blade (26). To accomplish this, integral pin features (not shown) extending inwardly from respective projections (44) of clamp arm (28) pivotally secure a first portion of clamp arm (28) to a distally projecting tongue (46) of outer tube (40); while an inserted pin (48) pivotally secures a second portion of clamp arm (28) to a distally projecting tongue (50) of inner tube (42). Thus, tubes (40, 42) cooperate to pivot clamp arm (28) toward blade (26) when outer tube (40) is retracted proximally relative to inner tube (42). It should be understood that clamp arm (28) may be pivoted back away from blade (26) by translating outer tube (40) distally relative to inner tube (42). In an exemplary use, clamp arm (28) may be pivoted toward blade (26) to grasp, compress, seal, and sever tissue captured between clamp pad (36) and blade (26) as shown in FIG. 3A. Clamp arm (28) may also be pivoted away from blade (26), as shown in FIG. 3B, to release tissue from between clamp pad (36) and blade (26); and/or to perform blunt dissection of tissue engaging opposing outer surfaces of clamp arm (28) and blade (26). In some alternative versions, inner tube (42) translates while outer tube (40) remains stationary to provide pivotal movement of clamp arm (28).

As shown in FIGS. 1-2, shaft assembly (14) of the present example extends distally from handle assembly (12). A rotation control assembly (52) has a rotation control member in the form of rotation control knob (54), which is secured to a proximal portion of outer tube (40). Knob (54) is rotatable relative to body (18), such that shaft assembly (14) is rotatable about the longitudinal axis defined by outer tube (40), relative to handle assembly (12). Such rotation may provide rotation of end effector (16) and shaft assembly (30) unitarily, which also includes unitary rotation of acoustic waveguide (38) coupled with transducer assembly (30) within handle assembly (12). In some other versions, various rotatable features may simply be omitted and/or replaced with alternative rotatable features, if desired.

While the present shaft assembly (14) is generally rigid and linear, it will be appreciated that alternative shaft assemblies may include an articulation section (not shown) for deflecting end effector (16) at various lateral deflection angles relative to a longitudinal axis defined by outer tube (40). It will be appreciated that such an articulation section may take a variety of forms. By way of example only, such an articulation section may be configured in accordance with one or more teachings of U.S. Pat. No. 9,402,682, entitled "Articulation Joint Features for Articulation Surgical Device," issued Aug. 2, 2016, the disclosure of which is incorporated by reference herein. As another merely illustrative example, an articulation section may be configured in accordance with one or more teachings of U.S. Pat. No. 9,393,037, entitled "Surgical Instruments with Articulating Shafts," issued Jul. 19, 2016, and/or U.S. Pat. No. 9,095,367, entitled "Flexible Harmonic Waveguides/Blades for Surgical Instruments," issued Aug. 4, 2015, the disclosures of which are incorporated by reference herein. Various other suitable forms that an articulation section may take will be apparent to those of ordinary skill in the art in view of the teachings herein.

B. Exemplary Handle Assembly

As seen in FIGS. 1 and 2, handle assembly (12) is reusable as discussed above and comprises body (18) defined by a pair of complementary housings (56) joined together. Housings (56) collectively define pistol grip (20) and include a cord support base (58) through which cable (34) extends between transducer assembly (30) and generator (32). While body (18) includes pistol grip (20) in this example, it should be understood that any other suitable kind of grip may be used.

Waveguide (38) extends proximally through knob (54) and into body (18) to mechanically couple with transducer assembly (30). When waveguide (38) is sufficiently coupled with transducer assembly (30), ultrasonic vibrations that are generated by transducer assembly (30) are communicated along waveguide (38) to reach blade (26). In the present example, the distal end of blade (26) is located at a position corresponding to an anti-node associated with resonant ultrasonic vibrations communicated through waveguide (38), in order to tune the acoustic assembly to a preferred resonant frequency $f_o$ when the acoustic assembly is not loaded by tissue. When transducer assembly (30) is energized, the distal end of blade (26) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (30) of the present example is activated, these mechanical oscillations are transmitted through waveguide (38) to reach blade (26), thereby providing oscillation of blade (26) at the resonant ultrasonic frequency. Thus, when tissue is secured between blade (26) and clamp pad (36), the ultrasonic oscillation of blade (26) may simultaneously sever the tissue and denature the proteins in adjacent tissue cells, thereby providing a coagulative effect with relatively little thermal spread. In some versions, an electrical current may also be provided through blade (26) and/or clamp pad (36) to also seal the tissue.

Further exemplary features and operabilities for disposable and/or reusable portions of surgical instrument (10) will be described in greater detail below, while other variations will be apparent to those of ordinary skill in the art in view of the teachings.

C. Exemplary Torque Wrench

Figure 4:
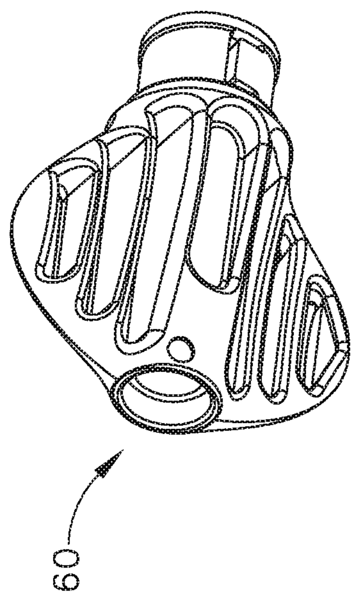
FIG. 4 depicts a perspective view of a torque wrench for coupling the shaft assembly of FIG. 1 to the handle assembly of FIG. 1.

In the present example, waveguide (38) is threadably secured to transducer assembly (30) for acoustically coupling waveguide (38) with transducer assembly (30) for use. In order to properly communicate the resonant ultrasonic vibrations from transducer assembly (30) to waveguide (38), a predetermined torque is applied to waveguide (38) during installation with transducer assembly (30). As seen in FIG. 4, a separate torque wrench (60) is used to couple the waveguide (38) with the transducer assembly (30) to inhibit overtightening of the waveguide (38). It should be understood that torque wrench (60) may ensure that a sufficient level of torque is used to couple waveguide (38) with transducer assembly (30) (i.e., to avoid separation of waveguide (38) from transducer assembly (30) while waveguide (38) and transducer assembly (30) are ultrasonically activated); while also preventing too much torque from being used to couple waveguide (38) with transducer assembly (30) (i.e., to avoid undue stress and the risk of breakage at the coupling of waveguide (38) from transducer assembly (30) while waveguide (38) and transducer assembly (30) are ultrasonically activated).

Torque wrench (60) of the present example may be slid proximally along shaft assembly (14) until torque wrench (60) engages knob (54), such that rotating torque wrench (60) similarly rotates knob (54), thereby rotating shaft assembly (14). During installation, a proximal end portion of waveguide (38) is received within a threaded bore (62) (see FIG. 10A) of transducer assembly (30). The operator rotates shaft assembly (14) via torque wrench (60), while holding handle assembly (12) stationary, thereby rotating waveguide (38) relative to transducer assembly (30). The proximal end portion of waveguide (38) is thus rotated into threaded engagement with transducer assembly (30). As installation torque increases during rotation, torque wrench (60) is configured to slip relative to knob (54) once the applied torque being transmitted therethrough exceeds the predetermined torque. In addition to slipping, torque wrench (60) generates audible and tactile "clicks" once the predetermined torque is achieved. Torque wrench (60) thus inhibits overtightening of waveguide (38) to transducer assembly (30). By way of further example only, torque wrench (60) may be configured and operable in accordance with at least some of the teachings of U.S. Pub. No. 2007/0191713, entitled "Ultrasonic Device for Cutting and Coagulating," published Aug. 16, 2007, now abandoned, the disclosure of which is incorporated by reference herein.

II. TRANSDUCER LOCK FOR COUPLING WAVEGUIDE WITH TRANSDUCER ASSEMBLY

As described above with respect to surgical instrument (10), once waveguide (38) and transducer assembly (30) are secured together at the predetermined torque, selective rotation of knob (54) collectively rotates the remainder of shaft assembly (14), end effector (16), waveguide (38), and transducer assembly (30) relative to handle assembly (12). However, even before proper installation at the predetermined torque, the proximal end of waveguide (38) may have enough frictional engagement with transducer assembly (30) to cause transducer assembly (30) to rotate with waveguide (38) relative to handle assembly (12). Such engagement may make it difficult, or even impossible in some cases, for a user to apply the predetermined torque for proper coupling of the waveguide (38) to transducer assembly (30), because the user may not be able to apply a reactionary torque to transducer assembly (30) up to the predetermined torque.

It may thus be desirable to inhibit rotation of transducer assembly (30) relative to waveguide (38) during coupling such that the user can effectively rotate the waveguide (38) relative to transducer assembly (30) to thereby secure waveguide (38) with transducer assembly (30) with the predetermined torque. More particularly, it may be desirable to selectively seize rotation of transducer assembly (30) relative to body (18) such that waveguide (38) may be effectively coupled within transducer assembly (30). The following description relates to various exemplary transducer locks (110, 210, 310, 410, 510, 610, 710) for use respective with surgical instruments (112, 212, 312, 412, 512, 612, 712) discussed below in greater detail. Accordingly, like numbers described herein indicate like features with respect to each exemplary transducer lock (110, 210, 310, 410, 510, 610, 710).

While transducer locks (110, 210, 310, 410, 510, 610, 710) are configured to selectively inhibit, and even prevent rotation of transducer assembly (30) relative to body (18), it will be appreciated that some rotation in alternative examples is possible in accordance with the invention. For example, alternative transducer locks may not strictly prevent rotation, but at least inhibit rotation enough to provide a reactionary torque equal to at least the predetermined torque for proper installation. The invention is thus not intended to be unnecessarily limited to preventing all relative rotation between transducer assembly (30) and body (18).

A. Exemplary Longitudinal Catch Lock

FIGS. 5A-9 illustrate a first exemplary transducer lock, in the form of a longitudinal catch lock (110) of a surgical instrument (112). Longitudinal catch lock (110) includes a lock switch (114) extending through a lock channel (116) in body (18). More particularly, lock channel (116) extends longitudinally through an upper surface (118) of body (18) directly above the longitudinal axis. Lock switch (114) is thus translatable between a distal, unlocked position and a proximal, locked position for respectively unlocking and locking rotation of transducer assembly (30) relative to body (18). While lock switch (114) and lock channel (116) are positioned on upper surface (118) of body (18) of the present example, it will be appreciated that lock switch (114) and lock channel (116) may be alternatively positioned so as to cooperate with transducer assembly (30). The invention is thus not intended to be unnecessarily limited to having lock switch (114) and lock channel (116) positioned as shown herein.

Figure 5A:
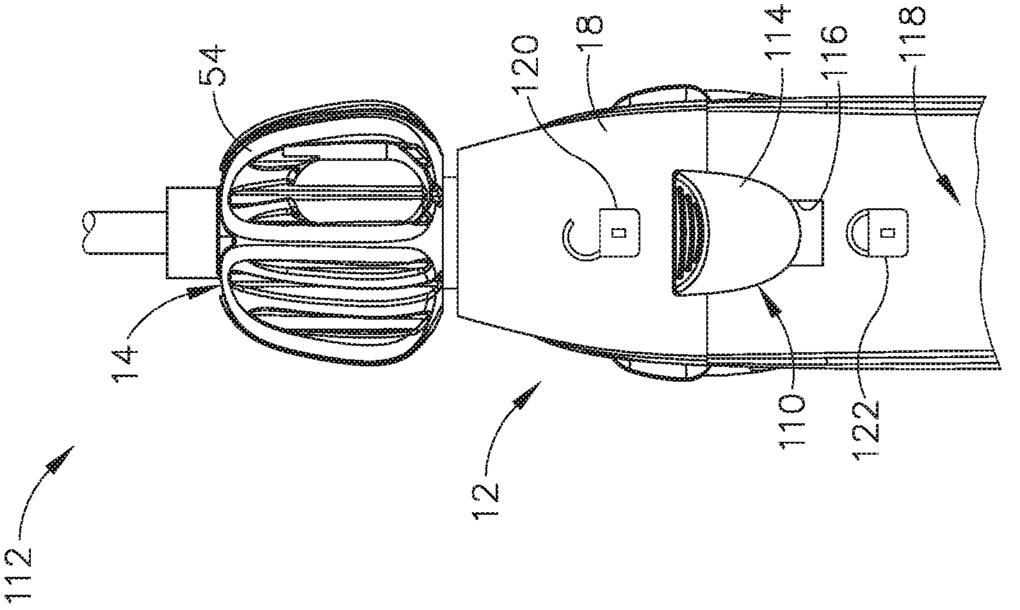
FIG. 5A depicts an enlarged top view of a longitudinal catch lock of the ultrasonic surgical instrument of FIG. 1 in an unlocked position.
Figure 5B:
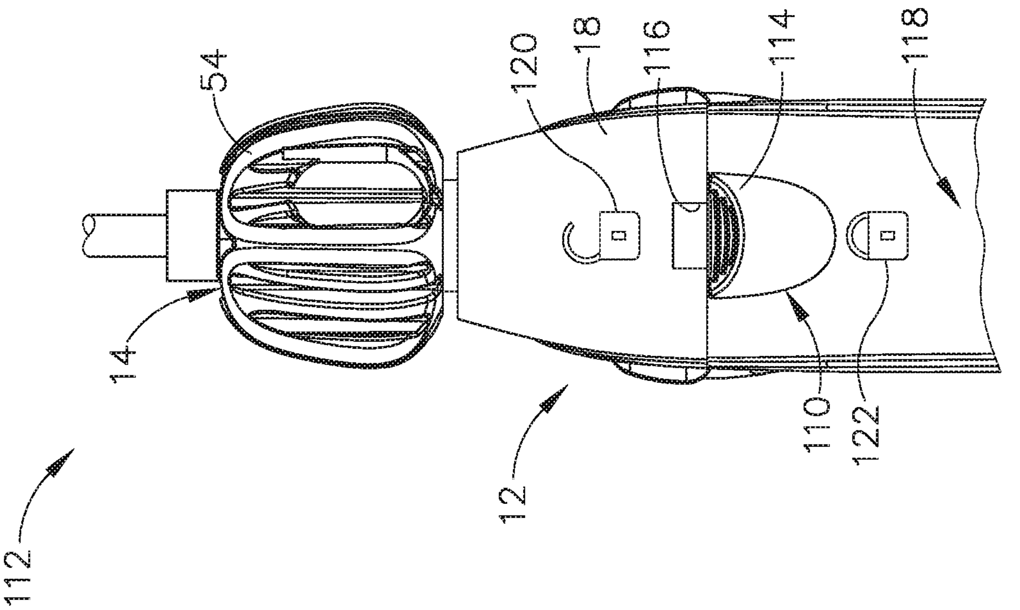
FIG. 5B depicts an enlarged top view of the longitudinal catch lock of FIG. 5A in a locked position.

As seen in FIGS. 5A-5B, upper surface (118) further includes an unlocked indicia (120) and a locked indicia (122) for visually indicating a rotational state (i.e., unlocked state or locked state) of transducer assembly (30) to the user. The present example has unlocked indicia (120) positioned adjacent to a distal end of lock channel (116), whereas locked indicia (122) is positioned adjacent to a proximal end of lock channel (116). Unlocked indicia (120) more particularly includes an image of an unlocked padlock, and locked indicia (122) more particularly includes an image of a locked padlock. However, it will be appreciated that these particular images and positions may vary in accordance with the invention herein and should not be unnecessarily limited to these particular unlocked and locked indicia (120, 122). Furthermore, longitudinal catch lock (110) may also include one or more cooperating detents (not shown) to releasably secure lock switch (114) in either of the unlocked and locked positions. The user may then manipulate other portions of surgical instrument (112) without necessarily holding lock switch (114) in the locked position. In some versions, lock switch (114) may be biased toward the unlocked position such that the user would hold lock switch (114) in the locked position while coupling with waveguide (38). The invention is thus not intended to be unnecessarily limited to either secured or biased lock switch (114) positions.

Figure 6A:
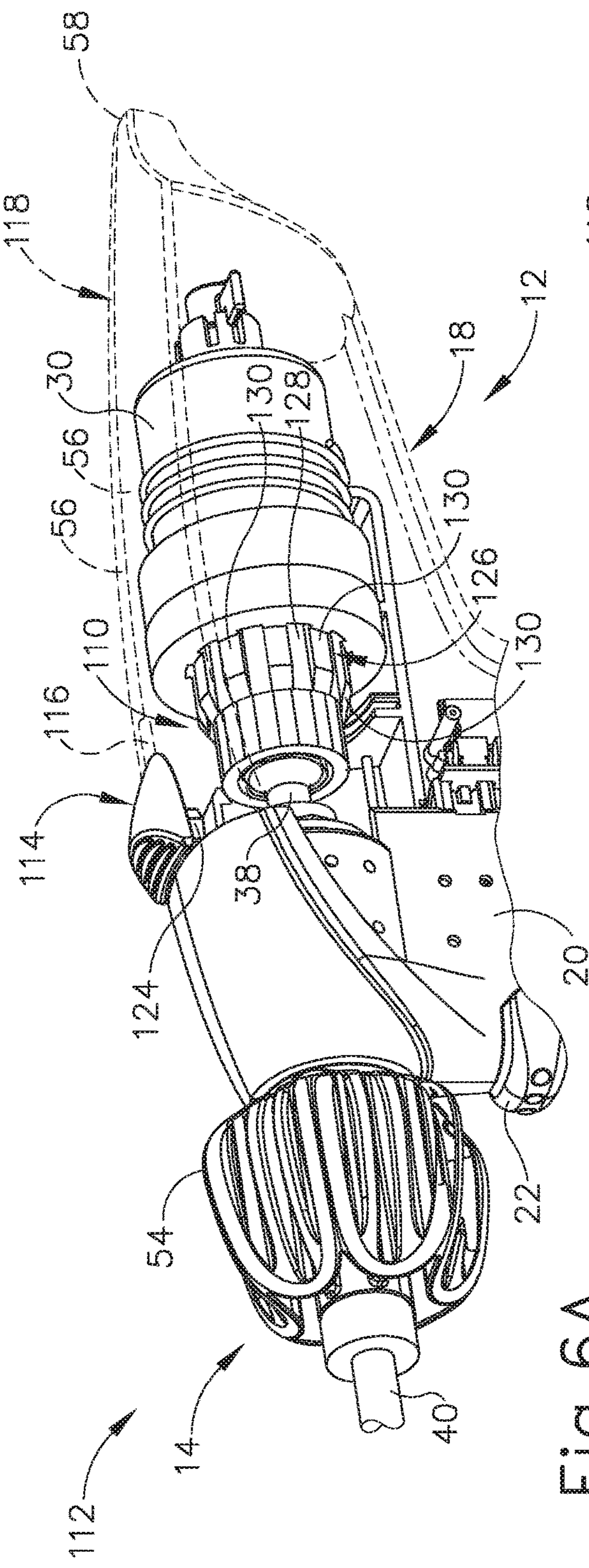
FIG. 6A depicts an enlarged perspective view of the handle assembly of FIG. 1 having various components removed for more clearly showing the ultrasonic transducer assembly and the longitudinal catch lock in the unlocked position.
Figure 6B:
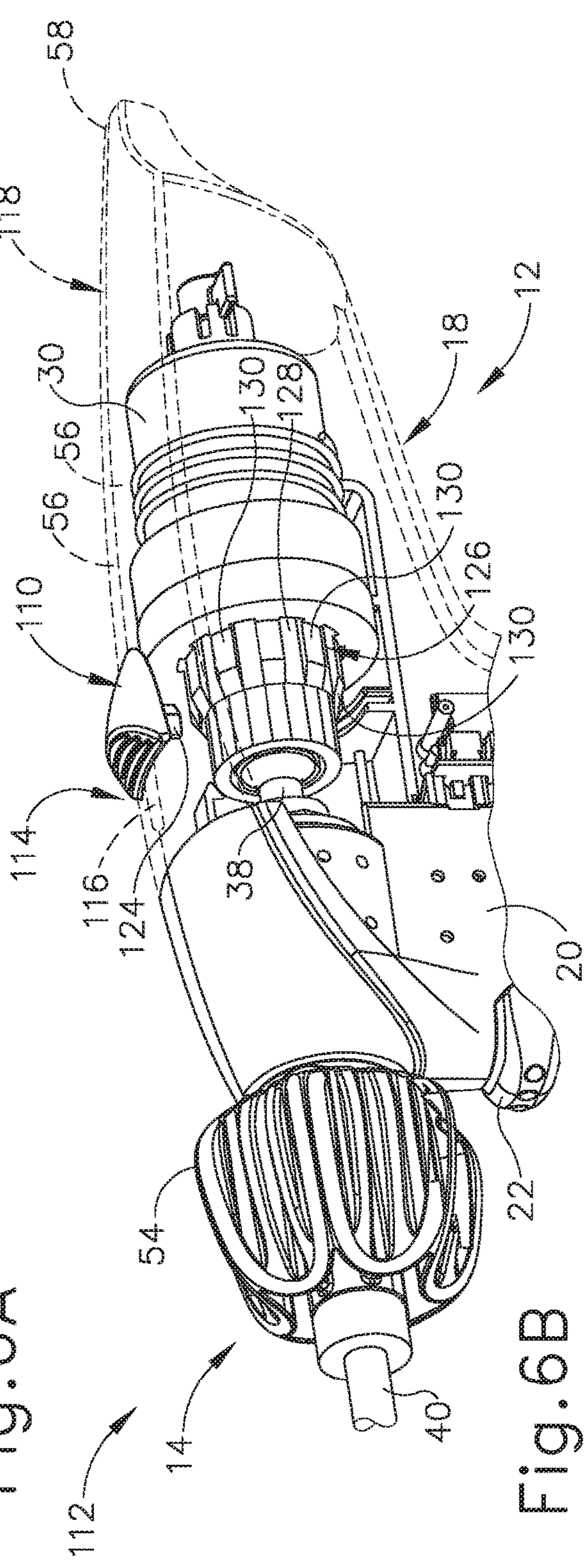
FIG. 6B depicts an enlarged perspective view of the handle assembly of FIG. 1 having various components removed for more clearly showing the ultrasonic transducer assembly and the longitudinal catch lock in the locked position.

As seen in FIGS. 6A and 6B, longitudinal catch lock (110) further includes an arrester (124) operatively connected to lock switch (114) and an engagement feature (126) operatively connected to transducer assembly (30) that cooperate together to selectively allow or inhibit rotation of transducer assembly (30) relative to body (18). To this end, arrester (124) extends transversely downwardly from lock switch (114) toward the longitudinal axis and, in the unlocked position, is distally offset from engagement feature (126) and transducer assembly (30). Engagement feature (126) of the present example is particularly in the form of an engagement collar (126) having an annular collar body (128) and a plurality of teeth (130) positioned angularly about annular collar body (128). Each tooth (130) extends radially outwardly from annular collar body (128) such that any pair of teeth (130) is configured to receive at least a portion of arrester (124) therebetween. Furthermore, engagement collar (126) is rigidly secured to a distal end portion of transducer assembly (30) and positioned concentrically about the longitudinal axis. Engagement collar (126) is thus rotatably fixed relative to transducer assembly (30) such that each may either rotate together relative to body (18) or be rotatably secured together relative to body (18).

Figure 7A:
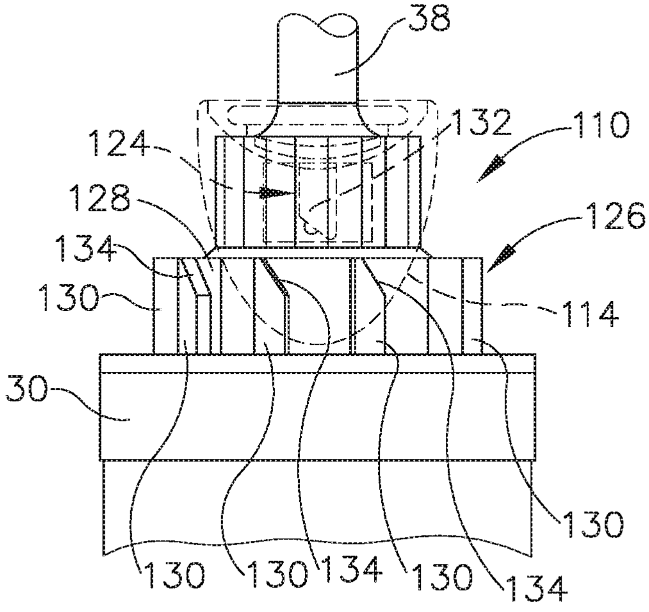
FIG. 7A depicts an enlarged top view of the longitudinal catch lock of FIG. 5A in the unlocked position.
Figure 7B:
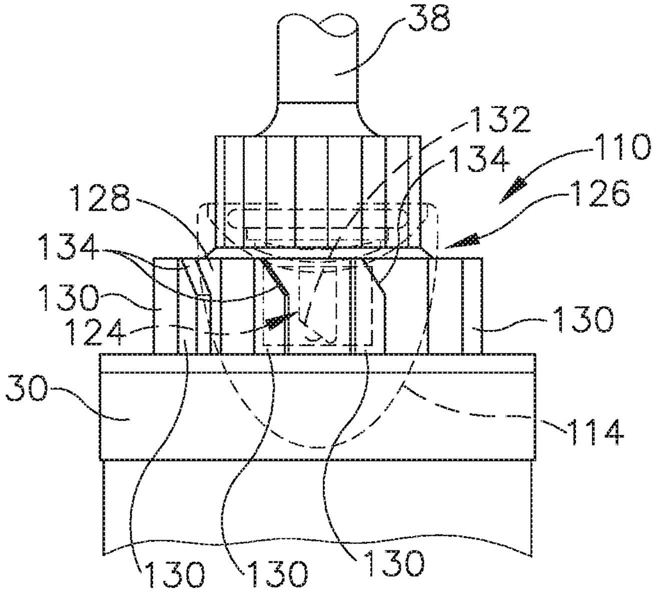
FIG. 7B depicts an enlarged top view of the longitudinal catch lock of FIG. 5A in the locked position.
Figure 8:
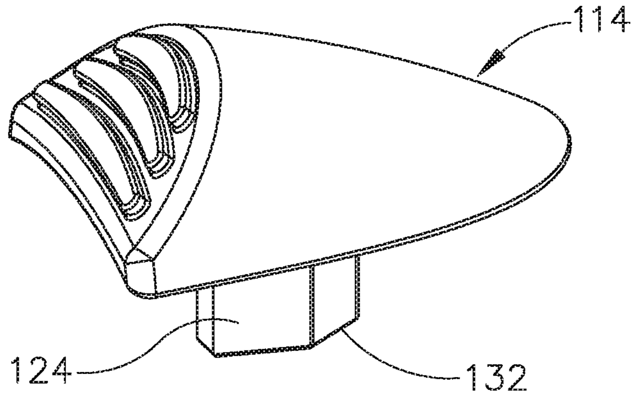
FIG. 8 depicts an upper perspective view of a lock switch and an arrester of the longitudinal catch lock of FIG. 5A.
Figure 9:
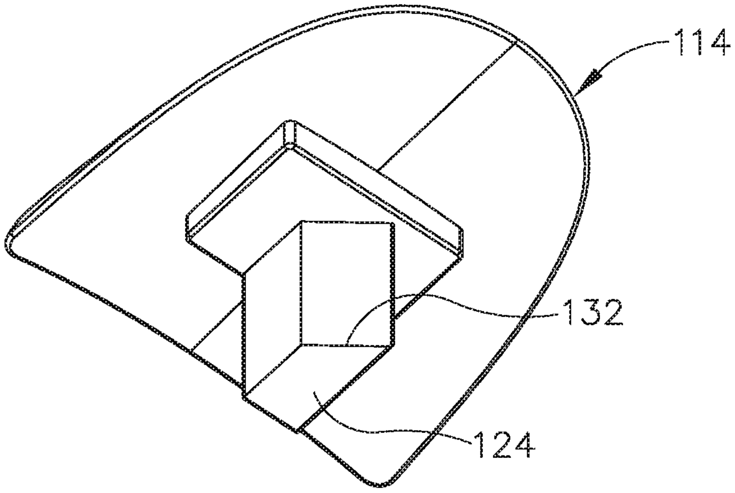
FIG. 9 depicts a lower perspective view of the lock switch and the arrester of FIG. 8.

FIGS. 6A and 7A illustrate lock switch (114) in the distal, unlocked position with arrester (124) in a distal, disengaged position, offset from engagement collar (126). Proximally translating lock switch (114) from the unlocked position toward the locked position similarly translates arrester (124) proximally from the disengaged position toward the engaged position shown in FIGS. 6B and 7B. In the engaged position, arrester (124) aligns between teeth (130) such that arrester (124) effectively engages teeth (130) to seize rotation of engagement collar (126) relative to body (18). In turn, engagement collar (126) inhibits further rotation of transducer assembly (30) relative to body (18).

In addition, as shown in FIGS. 7A-9, arrester (124) has a drive cam surface (132), while each tooth (130) has a driven cam surface (134). Drive and driven cam surfaces (132, 134) cooperate such that drive cam surface (132), while moving toward the engaged position, urges drive cam surface (134) to slightly rotate engagement collar (126). Such slight rotation rotates one or more teeth (130) out of longitudinal alignment with arrester (124) in order to guide arrester (124) between teeth (130) to the engaged position. Thus, drive and driven cam surfaces (132, 134) are configured to properly align engagement collar (126) with arrester (124) and inhibit one or more teeth from essentially blocking the proximal movement of arrester (124) to the engaged position.

In use, and with respect to FIGS. 1-7B, shaft assembly (14) is initially uncoupled from transducer assembly (30). The user translates lock switch (114) proximally from the unlocked position to the locked position such that arrester (124) engages engagement collar (126) to seize rotation of transducer assembly (30) relative to body (18). The user then introduces the proximal end portion of waveguide (38) into threaded bore (62) and rotates knob (54) via torque wrench (60) in a tightening direction to threadably engage the proximal end portion of waveguide (38) with transducer assembly (30). Even as frictional engagement between the waveguide (38) and transducer assembly (30) increases, in turn increasing applied torque, arrester (124) continues to block rotation of teeth (130) on engagement collar (126). The user thus continues to tighten waveguide (38) into transducer assembly (30) until reaching the predetermined torque. Once reaching the predetermined torque, torque wrench (60) slips to inhibit further tightening of waveguide (38) to transducer assembly (30); and "clicks" to further indicate to the user that the appropriate torque has been achieved. The user then removes torque wrench (60) from shaft assembly (14) and translates lock switch (114) distally to the unlocked position to free rotation of the transducer assembly (30) and waveguide (38) relative to body (18) for selective rotation during a surgical procedure. While the above use is described with respect to longitudinal catch lock (110) of surgical instrument (112), it will be appreciated that similar features of alternative transducer locks (210, 310, 410, 510, 610, 710) may be similarly used for preparing surgical instruments (212, 312, 412, 512, 612, 712) for use during a surgical procedure.

B. Exemplary Transverse Catch Lock

FIGS. 10A-11B illustrate a second exemplary transducer lock, in the form of a transverse catch lock (210) of a surgical instrument (212). Transverse catch lock (210) includes a lock switch (214) extending through a lock channel (216) in body (18). More particularly, lock channel (216) extends transversely through an upper surface (118) of body (18) directly above the longitudinal axis. Lock switch (214) is thus transversely translatable between an upper, unlocked position and a lower, locked position for respectively unlocking and locking rotation of transducer assembly (30). Given that lock switch (214) is generally depressed in use so as to be transversely translatable, lock switch (214) may also be referred to herein as a lock button. While lock switch (214) and lock channel (216) are positioned on upper surface (118) of body (18) of the present example, it will be appreciated that lock switch (214) and lock channel (216) may be alternatively positioned so as to cooperate with transducer assembly (30). The invention is thus not intended to be unnecessarily limited to having lock switch (214) and lock channel (216) positioned as shown herein.

Furthermore, transverse catch lock (210) includes a spring (220) that biases lock switch (214) toward the upper, unlocked position. Spring (220) is resiliently compressed between an upper mount (221) and a lower mount (222). Upper mount (221) is fixed to lock switch (214), whereas lower mount (222) is fixed to an interior of body (18). Spring (220) thus resiliently biases upper mount (221) and lock switch (214) upward such that upper mount (221) abuts against body (18). Depressing lock switch (214) downwardly toward the longitudinal axis causes lock switch (214) to translate downwardly through lower mount (222) to the locked position. By way of example only, the user may generally maintain depression of lock switch (214) to retain lock switch (214) in the locked position during coupling of waveguide (38) with transducer assembly (30). Of course, alternative examples may use various detents or other structures for releasably securing the position of lock switch (214) as desired. The invention is thus not intended to be unnecessarily limited to either secured or biased lock switch (214) positions.

Figure 11B:
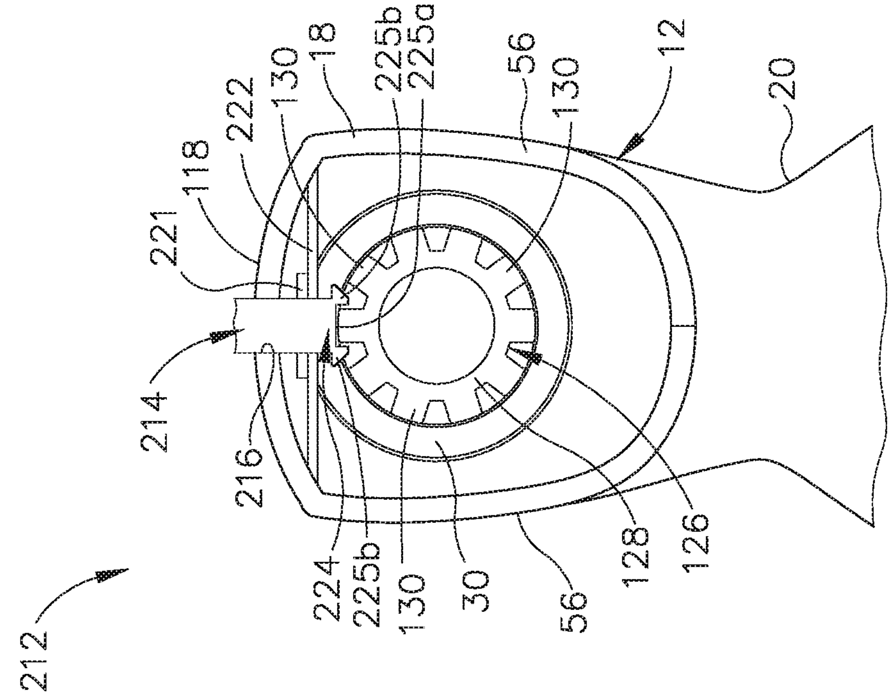
FIG. 11B depicts a cross-sectional view of the ultrasonic surgical instrument of FIG. 10B, taken along section line 11B-11B of FIG. 10B, with the transverse catch lock in the locked position.
Figure 11A:
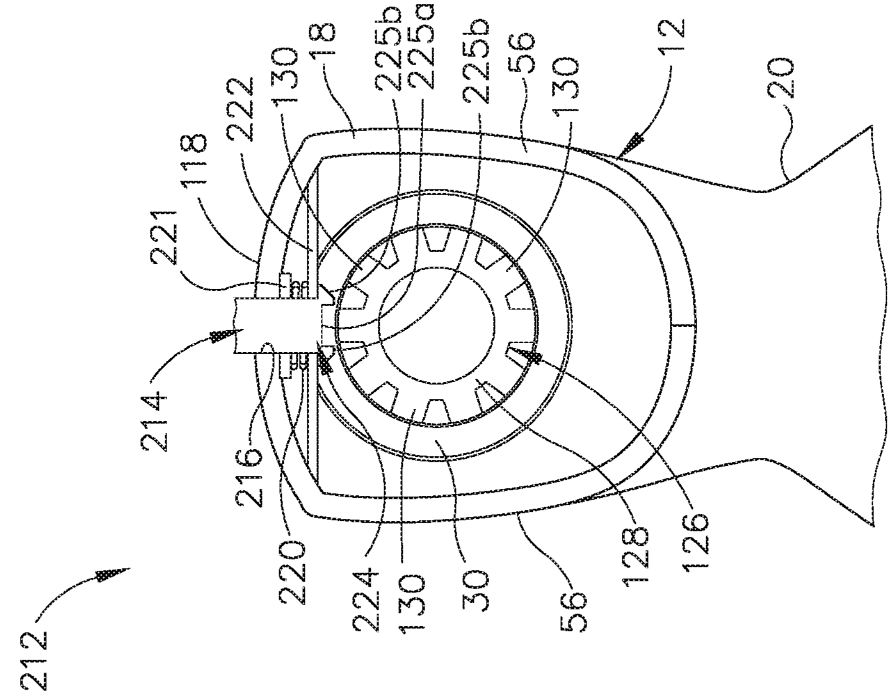
FIG. 11A depicts a cross-sectional view of the ultrasonic surgical instrument of FIG. 10A, taken along section line 11A-11A of FIG. 10A, with the transverse catch lock in the unlocked position.

As seen in FIG. 11A, transverse catch lock (210) further includes an arrester (224) operatively connected to lock switch (214) and engagement collar (126) operatively connected to transducer assembly (30) as discussed above. To this end, arrester (224) extends transversely downwardly from lock switch (214) toward the longitudinal axis and, in the unlocked position, is transversely offset from engagement collar (126) and transducer assembly (30). Arrester (224) includes a lower recess (225*a*) positioned between a pair of transversely extending catch members (225*b*). Catch members (225*b*) are configured to be positioned between respective pairs of teeth (130) of engagement collar (126), whereas lower recess (225*a*) is configured to receive a tooth (130) therein. Thereby, catch members (225*b*) are configured to capture tooth (130) within lower recess (225*a*).

Figure 10A:
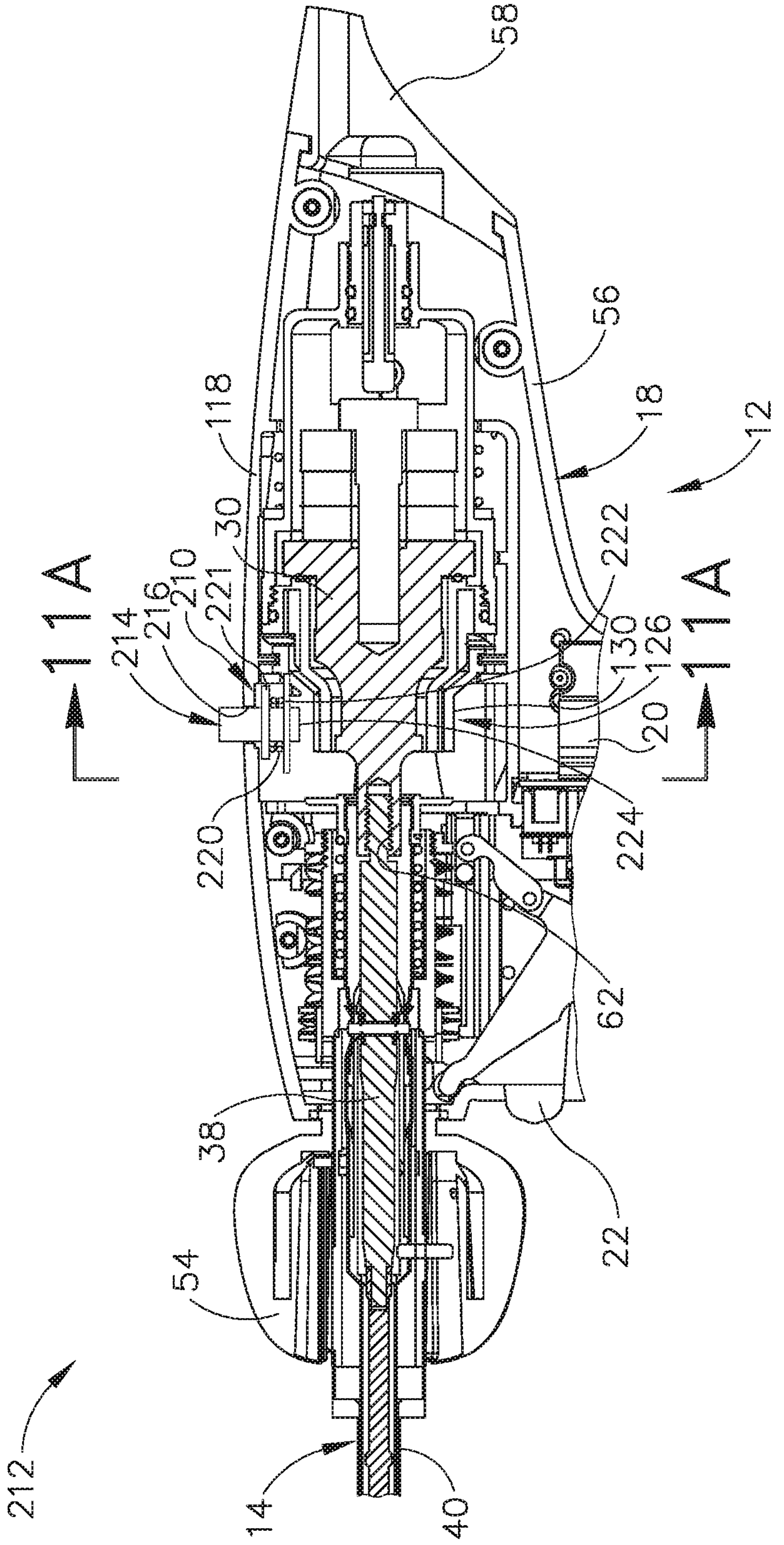
FIG. 10A depicts a side sectional view of a second exemplary ultrasonic surgical instrument having a transverse catch lock, taken along a centerline of an ultrasonic transducer assembly, the transverse catch lock being in an unlocked position.
Figure 10B:
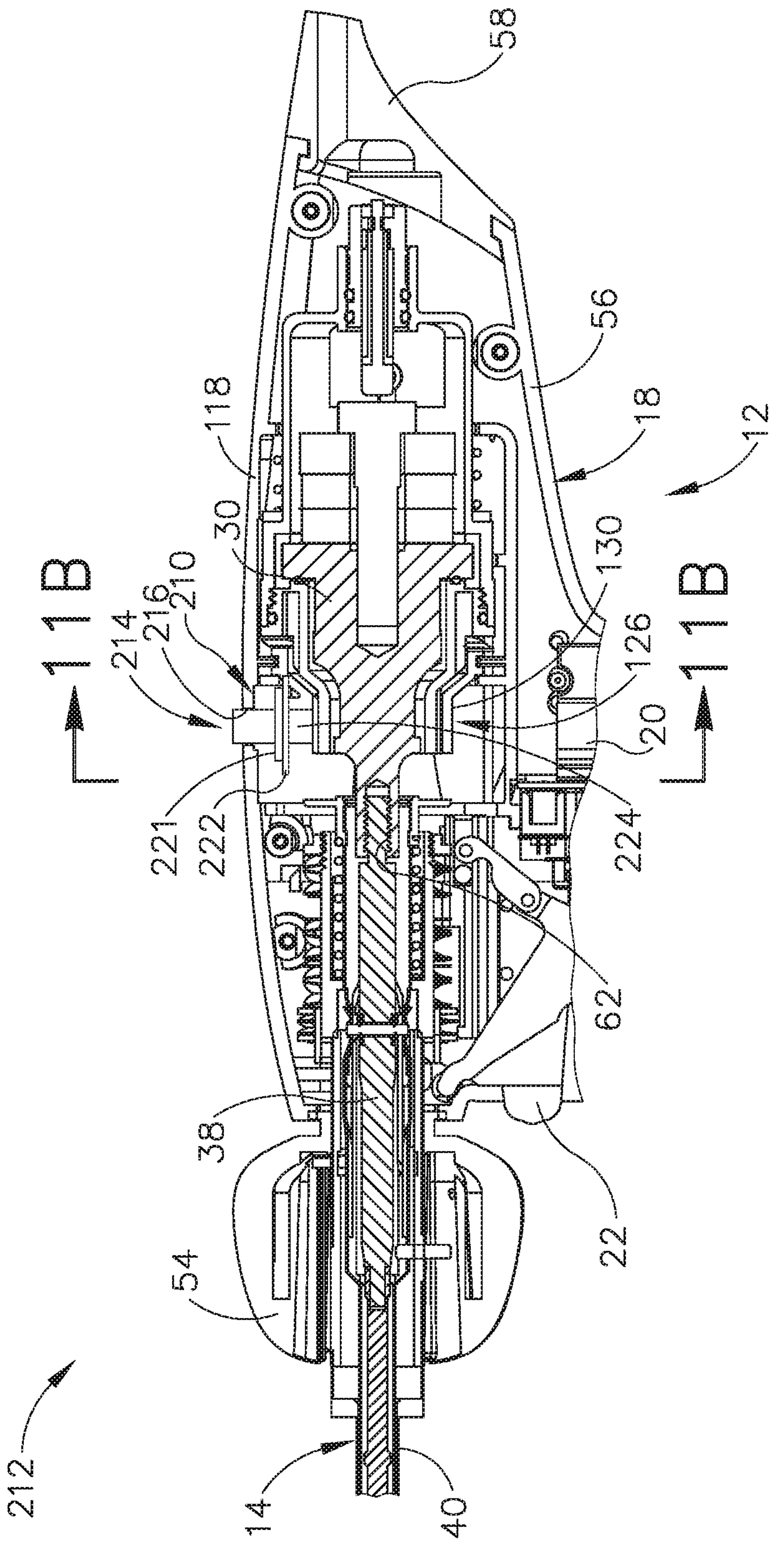
FIG. 10B depicts a side sectional view of the ultrasonic surgical instrument of FIG. 10A, taken along a centerline of the ultrasonic transducer assembly, the transverse catch lock being in a locked position.

FIGS. 10A and 11A illustrate lock switch (214) in the upper, unlocked position with arrester (224) in an upper, disengaged position, offset from engagement collar (126). Proximally translating lock switch (214) from the unlocked position toward the locked position similarly translates arrester (224) downward from the disengaged position toward a lower, engaged position shown in FIGS. 10B and 11B. In the engaged position, catch members (225*b*) of arrester (224) align between teeth (130) such that one tooth (130) is captured in lower recess (225*a*) to seize rotation of engagement collar (126) relative to body (18). In turn, engagement collar (126) inhibits further rotation of transducer assembly (30) relative to body (18).

C. Exemplary Bolt Catch Lock

FIGS. 12A-14B illustrate a third exemplary transducer lock, in the form of a bolt catch lock (310) of a surgical instrument (312). Bolt catch lock (310) includes a lock switch (314) extending through a lock channel (316) in body (18). More particularly, lock channel (316) extends longitudinally and laterally through an upper surface (118) of body (18). Lock switch (314) is thus pivotally and longitudinally translatable between a distal, unlocked position and a proximal, locked position for respectively unlocking and locking rotation of transducer assembly (30) as shown respectively in FIGS. 12A and 12B. While lock switch (314) and lock channel (316) are positioned on upper surface (118) of body (18) of the present example, it will be appreciated that lock switch (314) and lock channel (216) may be alternatively positioned so as to cooperate with transducer assembly (30). The invention is thus not intended to be unnecessarily limited to having lock switch (314) and lock channel (316) positioned as shown herein. The relative movement of lock switch (314) through lock channel (316) may also be referred to as a bolt action movement as illustrated with respect to FIGS. 12A-13B. To this end, lock channel (316) has a distal lateral slot (317*a*), an intermediate longitudinal slot (317*b*), and a proximal lateral slot (317*c*) through which to move lock switch (314) from the unlocked position to the locked position and vice versa.

Figure 14A:
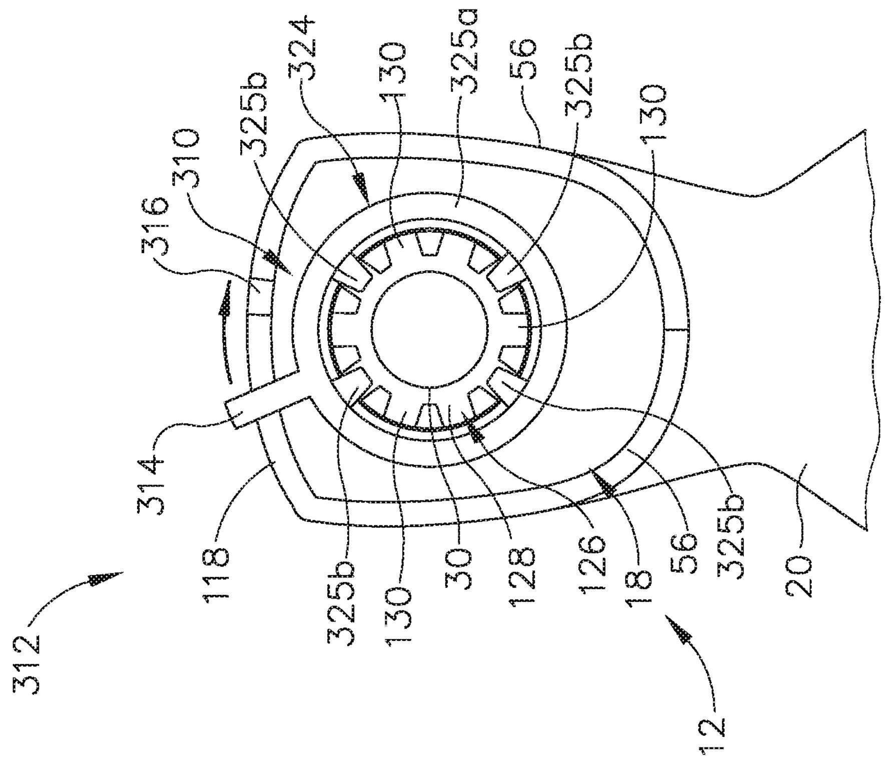
FIG. 14A depicts a cross-sectional view of the ultrasonic surgical instrument of FIG. 12A, taken along section line 14A-14A of FIG. 13A, with the bolt catch lock in the unlocked position.
Figure 14B:
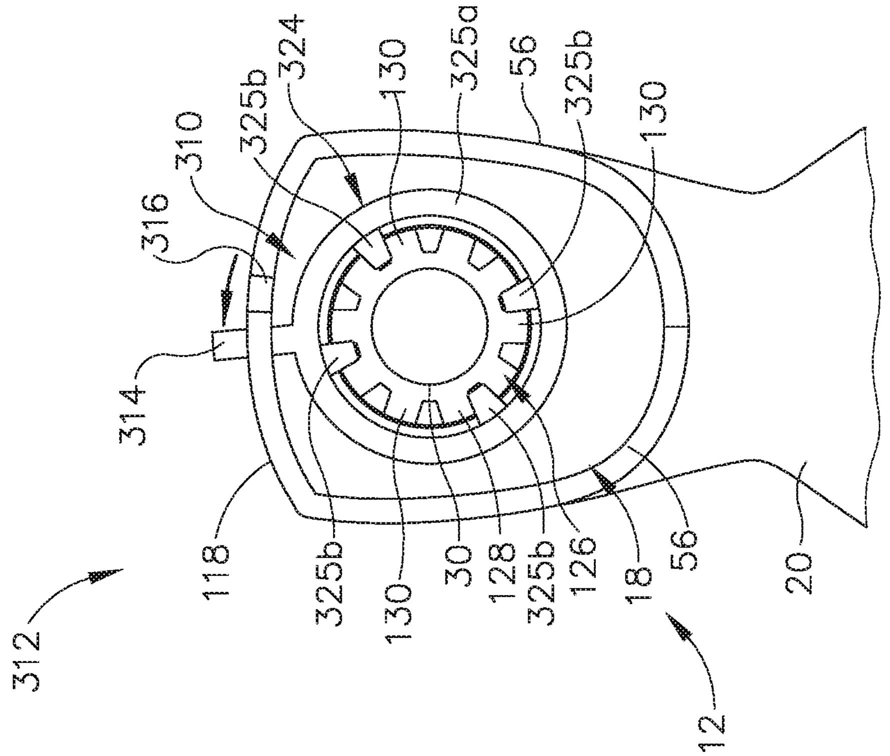
FIG. 14B depicts a cross-sectional view of the ultrasonic surgical instrument of FIG. 12A, taken along section line 14B-14B of FIG. 13B, with the bolt catch lock in the locked position.

As seen in FIGS. 14A and 14B, bolt catch lock (110) further includes an arrester (324) operatively connected to lock switch (314) and engagement collar (126) operatively connected to transducer assembly (30) as discussed above. To this end, arrester (324) extends transversely downwardly from lock switch (214) and has an annular body (325*a*) surrounding and concentrically positioned along the longitudinal axis. In the unlocked position, arrester (324) is distally offset from engagement collar (126) and transducer assembly (30). Arrester (324) further includes a plurality of catch members (325*b*) angularly positioned about the annular body (325*a*) and extending radially inwardly toward the longitudinal axis. Such catch members (325*b*) may also be referred to as inner teeth. Catch members (325*b*) are configured to be received between respective pairs of teeth (130) of engagement collar (126) for cooperative engagement therebetween in the locked position.

Figure 13B:
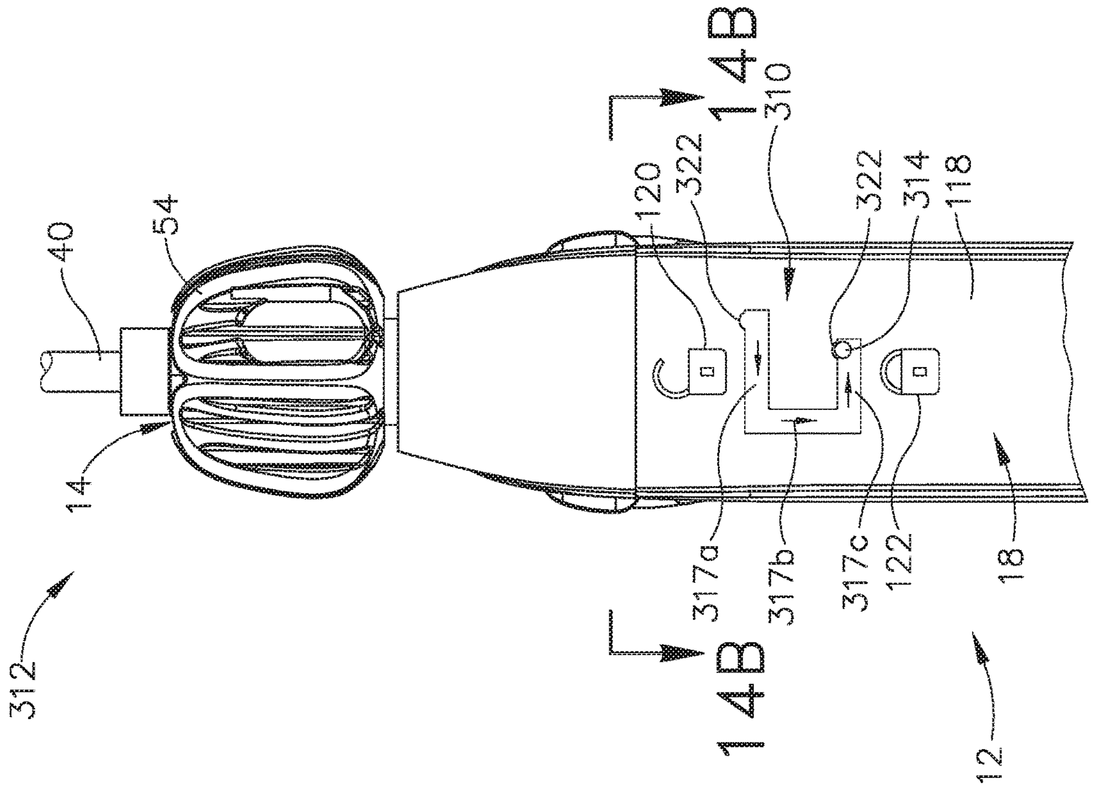
FIG. 13B depicts the enlarged top view of the bolt catch lock of FIG. 12A in the locked position.
Figure 13A:
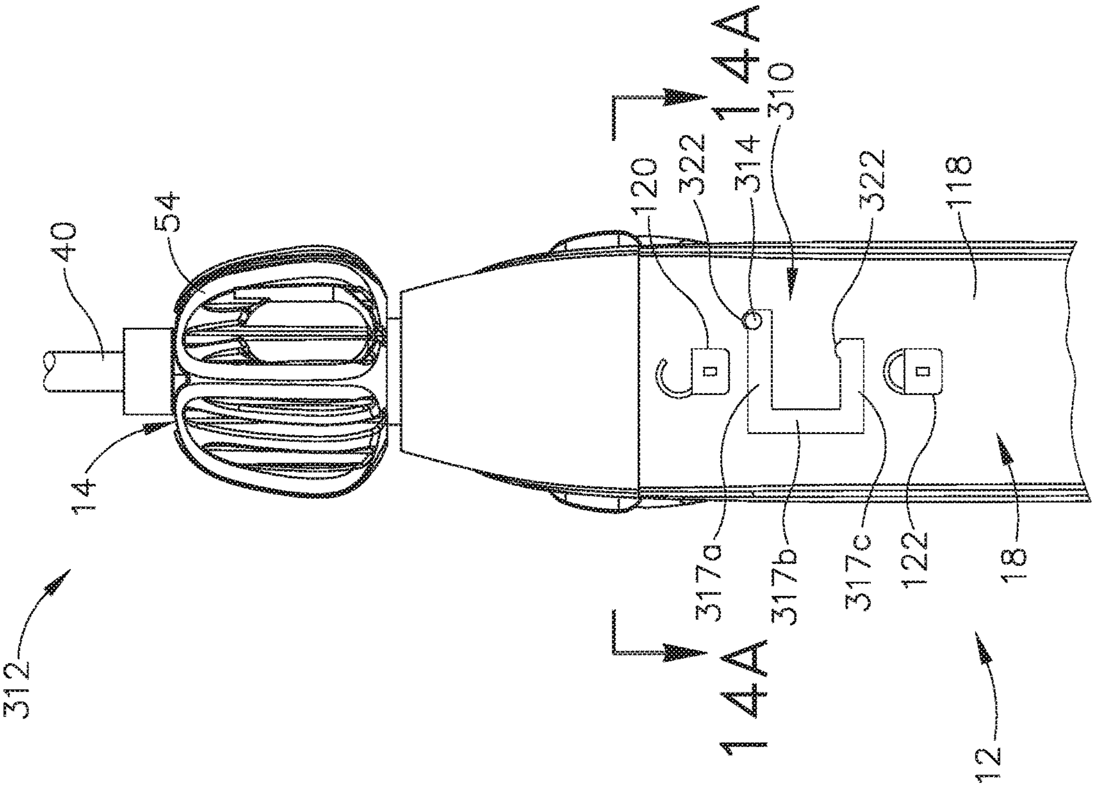
FIG. 13A depicts an enlarged top view of the bolt catch lock of FIG. 12A in the unlocked position.

Bolt catch lock (310) also includes a spring (320) shown in FIGS. 13A and 13B that biases lock switch (314) toward the distal, unlocked position. Spring (320) is resiliently compressed between an interior portion of body (18) and annular body (325*a*) of arrester (324). Spring (320) thus resiliently biases arrester (324) and lock switch (314) distally such that lock switch (314) is positioned distally in either distal slot (317*a*) of lock channel (316) or proximal slot (317*c*) of lock channel (316). By way of example, each of distal and proximal slots (317*a*, 317*c*) has a distal detent (322) configured to receive lock switch (318) in the unlocked and locked positions. Each distal detent (322) thus releasably captures lock switch (318) to secure lock switch (318) without further grip by the user. Of course, the user may urge lock switch (318) from either distal detent (322) for bolt action movement as desired in the present example. Alternative examples may use various detents or other structures for simply biasing the position of lock switch (314) as desired. The invention is thus not intended to be unnecessarily limited to either secured or biased lock switch (314) positions.

Figure 12A:
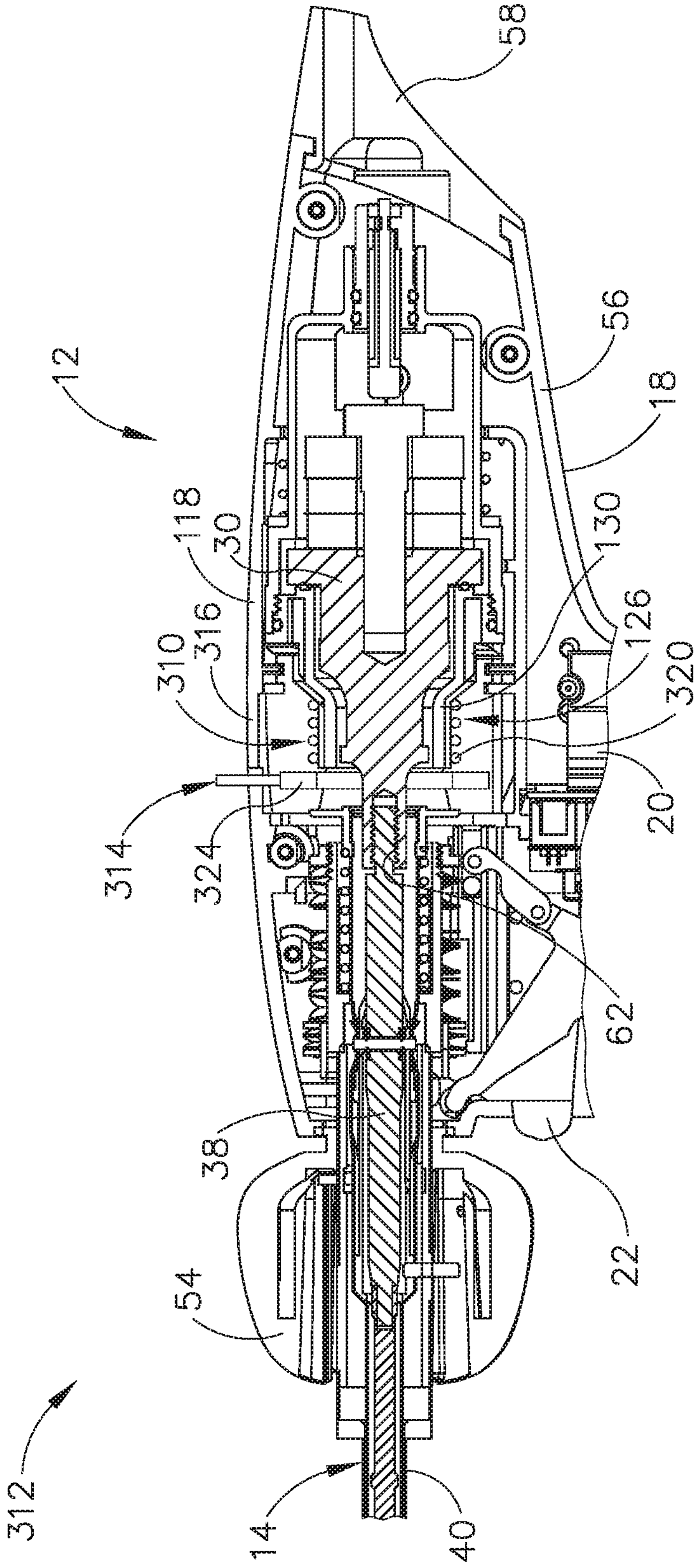
FIG. 12A depicts a side sectional view of a third exemplary ultrasonic surgical instrument having a bolt catch lock, taken along a centerline of an ultrasonic transducer assembly, the bolt catch lock being in an unlocked position.
Figure 12B:
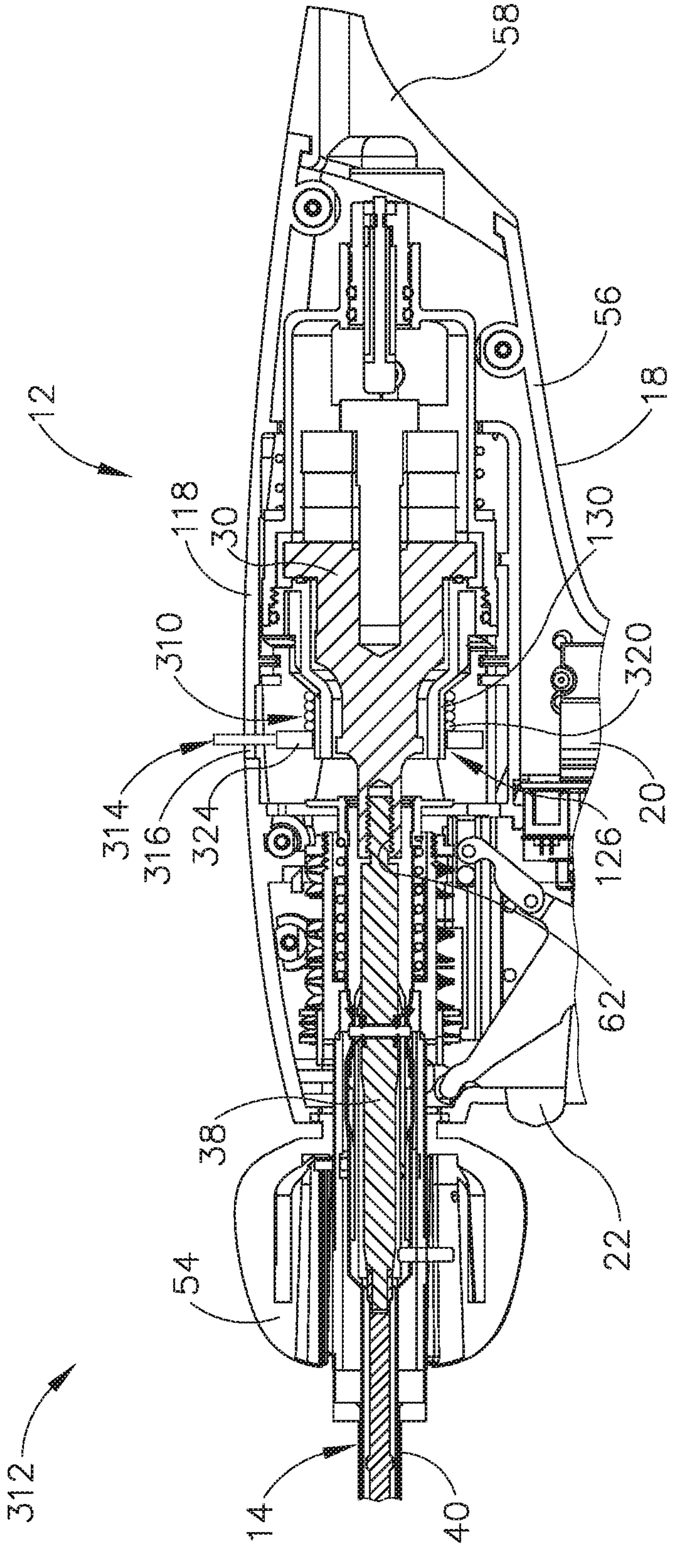
FIG. 12B depicts the side sectional view of the ultrasonic surgical instrument of FIG. 12A, taken along a centerline of the ultrasonic transducer assembly, the bolt catch lock being in a locked position.

FIGS. 12A, 13A, and 14A illustrate lock switch (314) in the distal, unlocked position with arrester (324) in a distal, disengaged position, offset from engagement collar (126). As discussed briefly above, the user directs bolt catch lock (310) through bolt action movement between the unlocked and locked positions. Specifically, pivoting lock switch (314) as shown in FIG. 14A pivots lock switch (314) from the locked position to a junction of the distal and intermediate slots (317*a*, 317*b*). Simultaneously, arrester (324) pivots about longitudinal axis without translating longitudinally. The user then translates lock switch (314) proximally through intermediate slot to proximally direct catch members (325*b*) into engagement with teeth (130) of engagement collar (126) as shown in FIGS. 12B and 14B. From the junction of intermediate slot (317*b*) and proximal slot (317*c*), lock switch (314) pivots through proximal slot (317*c*) to the locked position in distal detent (322) as shown in FIG. 13B, while arrester (324) pivots with engagement collar (126) in the engaged position as shown in FIG. 14B. Engagement collar (126) thereby inhibits further rotation of transducer assembly (30) relative to body by being captured rotatably within arrester (324).

D. Exemplary Pivot Catch Lock

Figure 15A:
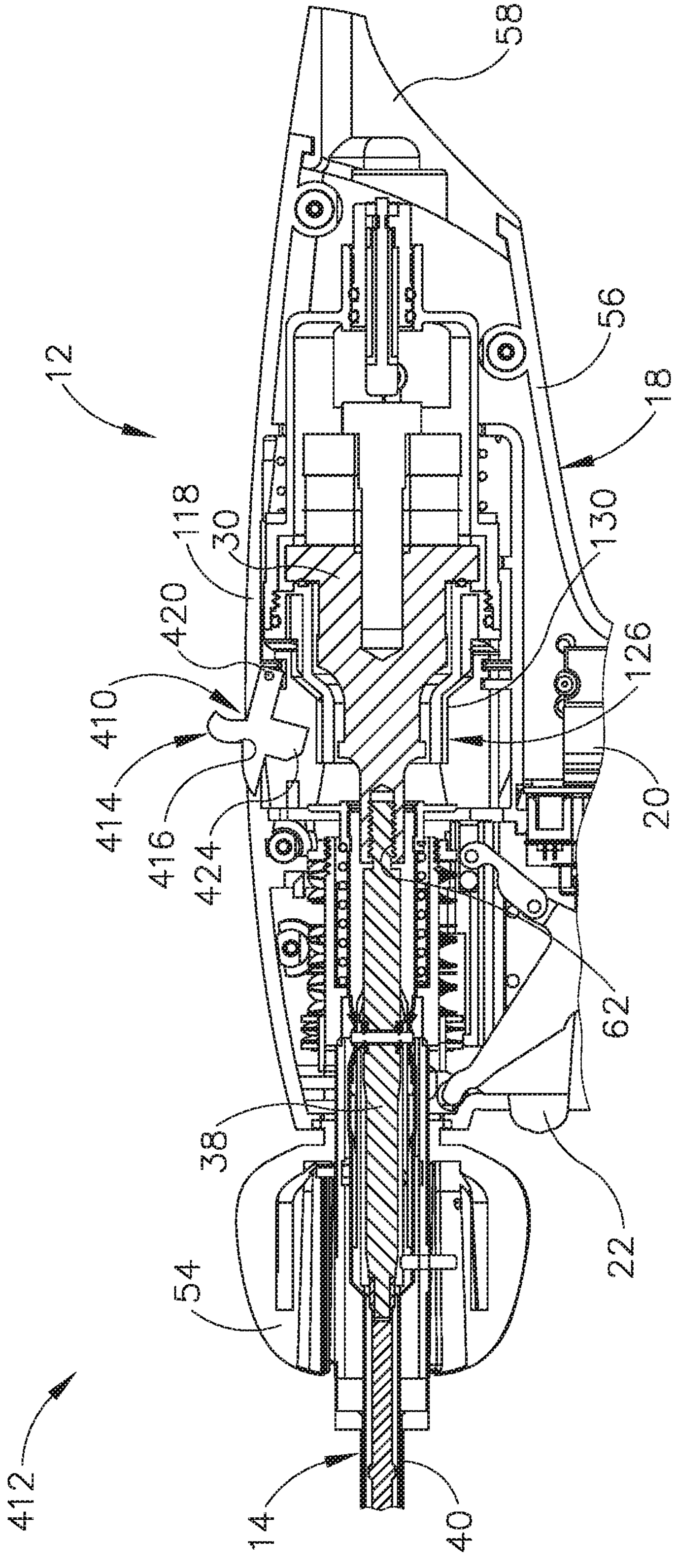
FIG. 15A depicts a side sectional view of a fourth exemplary ultrasonic surgical instrument having a pivot catch lock, taken along a centerline of an ultrasonic transducer assembly, the pivot catch lock being in an unlocked position.
Figure 15B:
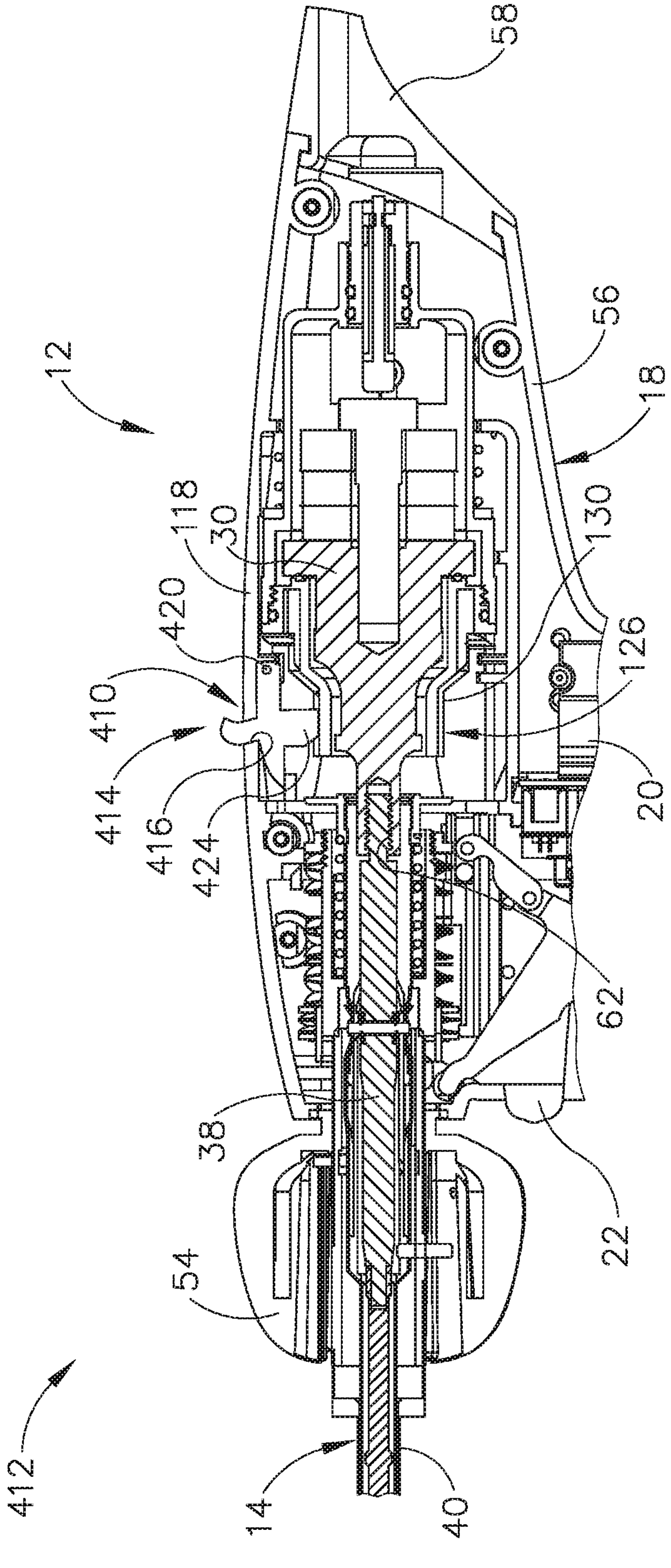
FIG. 15B depicts a side sectional view of the ultrasonic surgical instrument of FIG. 15A, taken along a centerline of the ultrasonic transducer assembly, the pivot catch lock being in a locked position.
Figure 16:
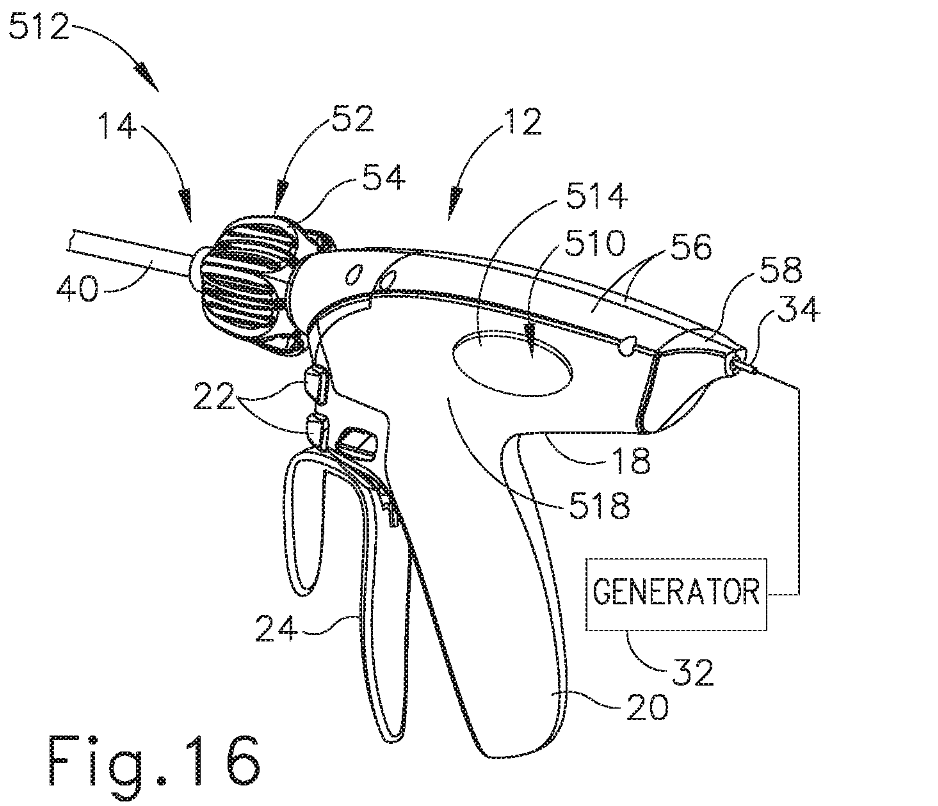
FIG. 16 depicts a perspective view of a fifth exemplary ultrasonic surgical instrument having a grip clamp lock.

FIGS. 15A-15B illustrate a fourth exemplary transducer lock, in the form of a pivot catch lock (410) of a surgical instrument (412). Pivot catch lock (410) includes a pivotally mounted lock switch (414) extending through a lock channel (416) in body (18). More particularly, lock channel (416) extends transversely through an upper surface (118) of body (18) directly above the longitudinal axis. Lock switch (414) is thus pivotable between an upper, unlocked position and a lower, locked position for respectively unlocking and locking rotation of transducer assembly (30). Given that lock switch (414) is generally depressed in use so as to pivot toward the longitudinal axis, lock switch (414) may also be referred to herein as a lock button. While lock switch (414) and lock channel (416) are positioned on upper surface (118) of body (18) of the present example, it will be appreciated that lock switch (414) and lock channel (416) may be alternatively positioned so as to cooperate with transducer assembly (30). The invention is thus not intended to be unnecessarily limited to having lock switch (414) and lock channel (416) positioned as shown herein.

Furthermore, pivot catch lock (410) includes a spring (420) that biases lock switch (414) toward the upper, unlocked position. In the present example, spring (420) is a torsional spring resiliently compressed between lock switch (414) and an interior of body (18). Spring (420) thus resiliently biases lock switch (414) upwardly such that an interior portion of lock switch (414) abuts against body (18). Depressing lock switch (414) downwardly toward the longitudinal axis causes lock switch (414) to pivot downwardly to the locked position. By way of example, the user may generally maintain depression of lock switch (414) to retain lock switch (414) in the locked position during coupling of waveguide (38) with transducer assembly (30). Of course, alternative examples may use various detents or other structures for releasably securing the position of lock switch (414) as desired. The invention is thus not intended to be unnecessarily limited to either secured or biased lock switch (414) positions.

Pivot catch lock (110) further includes an arrester (424) operatively connected to lock switch (414) and engagement collar (126) operatively connected to transducer assembly

(30) as discussed above. To this end, arrester (424) extends transversely downward from lock switch (414) toward the longitudinal axis and, in the unlocked position, is transversely offset from engagement collar (126) and transducer assembly (30). A lower end portion of arrester (424) is configured to be positioned between respective pairs of teeth (130) of engagement collar (126), thereby inhibiting relative movement therebetween.

FIG. 15A illustrates lock switch (414) in the upper, unlocked position with arrester (424) in an upper, disengaged position, offset from engagement collar (126). Pivoting lock switch (414) downwardly from the unlocked position toward the locked position similarly translates arrester (424) downwardly from the disengaged position toward a lower, engaged position shown in FIG. 15B. In the engaged position, the lower end portion of arrester (424) aligns between teeth (130) to engage at least one tooth (130) and seize rotation of engagement collar (126) relative to body (18). In turn, engagement collar (126) inhibits further rotation of transducer assembly (30) relative to body (18).

E. Exemplary Grip Clamp Lock

FIGS. 16-19B illustrate a fifth exemplary transducer lock, in the form of a grip clamp lock (510) of a surgical instrument (512). Grip clamp lock (510) includes a pair of lock switches (514) extending respectively through a pair of lock channels (516) in body (18). More particularly, lock channels (516) extend laterally through opposing side surfaces (518) of body (18) directly lateral from the longitudinal axis. Each lock switch (514) is thus translatable between an outer, unlocked position and an inner, locked position for respectively unlocking and locking rotation of transducer assembly (30) relative to body (18). In other words, each lock switch (514) is configured to be directed inwardly toward the longitudinal axis from the unlocked position to the locked position as shown in FIGS. 17A and 17B, respectively. Given that each lock switch (514) is generally depressed in use so as to be translate toward the longitudinal axis, lock switches (514) may also be referred to herein as lock buttons. While each lock switch (514) and lock channels (516) are positioned on side surfaces (518) of body (18) of the present example, it will be appreciated that lock switches (514) and lock channels (516) may be alternatively positioned so as to cooperate with transducer assembly (30). Furthermore, while the present example of grip clamp lock (510) has two lock switches (514), it will be appreciated that fewer or more such switches (514) may be used in alternative examples. The invention is thus not intended to be unnecessarily limited to having two lock switches (514) and two lock channels (516) positioned as shown herein.

Figure 18:
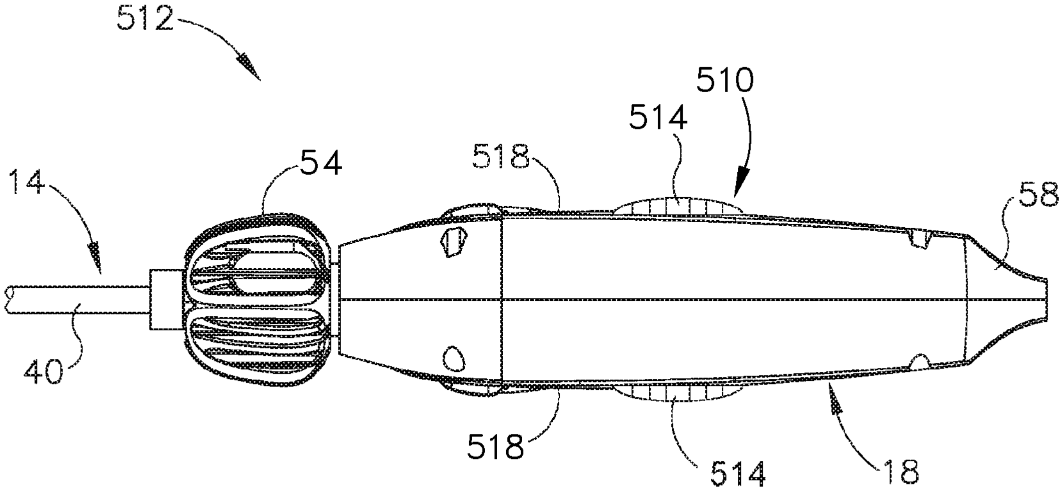
FIG. 18 depicts a top view of the ultrasonic surgical instrument of FIG. 16.
Figures 19A, 19B:
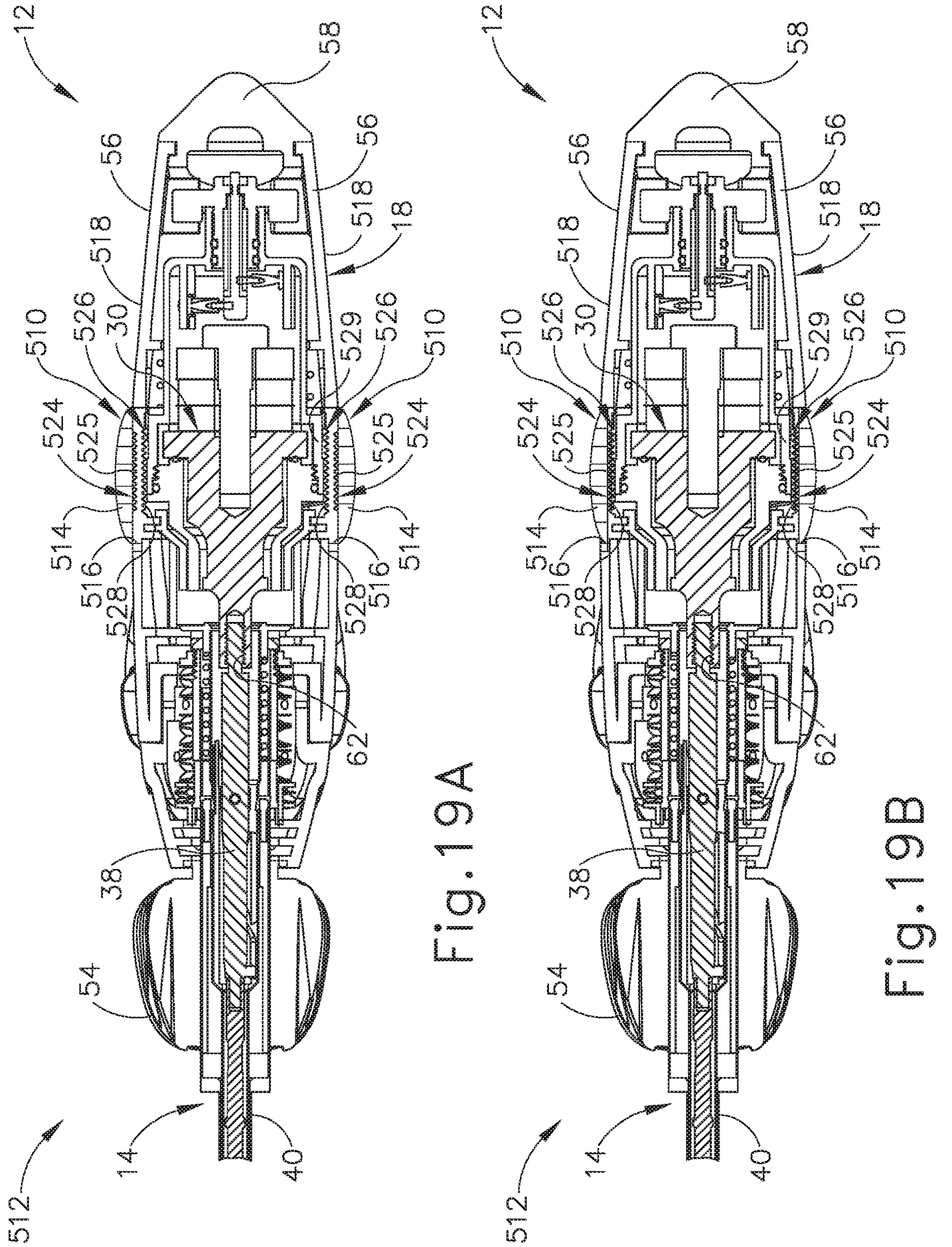
FIG. 19A depicts a top sectional view of the ultrasonic surgical instrument of FIG. 16, taken along a centerline of the ultrasonic transducer assembly, the grip clamp lock being in the unlocked position.
FIG. 19B depicts a top sectional view of the ultrasonic surgical instrument of FIG. 16, taken along a centerline of the ultrasonic transducer assembly, the grip clamp lock being in the locked position.

Each lock switch (514) is resiliently mounted in lock channels (516) by a biasing member (not shown), which urges each lock switch (514) toward the unlocked position. The user may generally maintain depression of each lock switch (514) to retain lock switches (514) in the locked position during coupling of waveguide (38) with transducer assembly (30). For example, the user may use one or more hands to selectively squeeze lock switches (514) simultaneously toward the locked position as shown in FIGS. 18-19B. Of course, alternative examples may use various detents or other structures for releasably securing the position of lock switches (514) as desired. The invention is thus not intended to be unnecessarily limited to either secured or biased lock switch (514) positions.

Grip clamp lock (510) further includes an arrester (524) operatively connected to lock switch (514) and an engagement feature (526) operatively connected to transducer assembly (30) that cooperate together to selectively allow or inhibit rotation of transducer assembly (30) relative to body (18). To this end, each arrester (524) extends laterally inwardly from each respective lock switch (514) toward the longitudinal axis and, in the unlocked position is laterally offset from engagement feature (526) and transducer assembly (30). By way of example, arrester (524) includes an abrasive, high-friction surface, such as a serrated surface (525). Serrated surface (525) faces inwardly toward longitudinal axis for engagement with engagement feature (526) as shown in FIGS. 19A and 19B.

As shown in FIGS. 17A, 17B, 19A, and 19B engagement feature (526) of the present example is particularly in the form of another serrated surface (528) rigidly fixed on a transducer housing (529) of transducer assembly (30). Serrated surface (528) generally covers an outer surface of transducer housing (529) such that serrated surface (528) surrounds the longitudinal axis. Serrated surface (528) also extends radially outwardly from the outer surface of transducer housing (529) for engagement with serrated surfaces (525) of each arrester (524). Engagement between serrated surfaces (525) of arresters (524) and serrated surface (528) of transducer housing (529) tends to inhibit relative rotation with a relatively high coefficient of friction therebetween. Moreover, increasing the inward depression force on each lock switch (514) in turn increases the compression force of serrated surfaces (525) of arresters (524) against serrated surface (528) of transducer housing (529) for increased friction. The user may thus apply more or less compression as desired for inhibiting rotation of transducer assembly (30). While the present example includes various serrated surfaces (525) for inhibiting relative rotation, it will be appreciated that alternative high-friction surfaces may also be so used. By way of further example, alternative structures extending respectively from arrester (524) and transducer housing (529) that cooperatively engage for inhibiting relative rotation may also be similarly configured. Accordingly, other structures for such engagement may be used with grip clamp lock (510), and the invention is not intended to be unnecessarily limited to the abrasive, high-friction, serrated surfaces (525, 528) described herein.

Figure 17A:
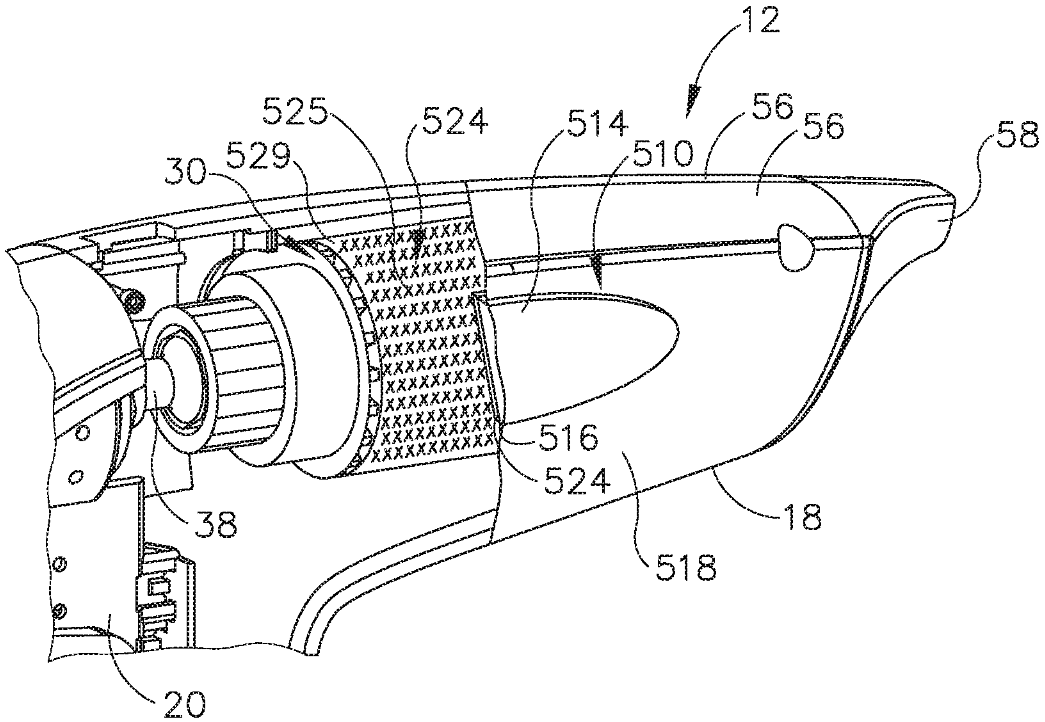
FIG. 17A depicts an enlarged perspective view of the ultrasonic surgical instrument of FIG. 16 having various components removed for more clearly showing an ultrasonic transducer assembly and the grip clamp lock in an unlocked position.
Figure 17B:
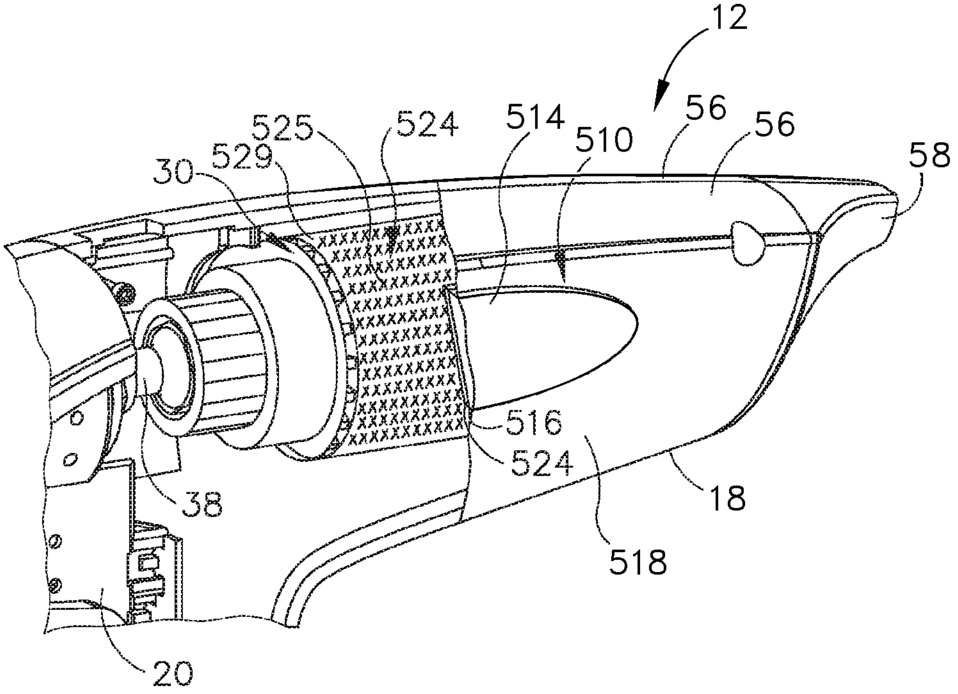
FIG. 17B depicts an enlarged perspective view of the ultrasonic surgical instrument of FIG. 16 having various components removed for more clearly showing the ultrasonic transducer assembly and the grip clamp lock in a locked position.

FIGS. 17A and 19A illustrate lock switches (514) in the laterally outward, unlocked position with arrester (524) in a laterally outward, disengaged position, which is offset from serrated surface (528) of transducer housing (529). Laterally translating lock switches (514) inwardly from the unlocked position toward the locked position similarly translates arrester (524) inward from the disengaged position toward an engaged position shown in FIGS. 17B and 19B. In the engaged position, serrated surfaces (525) of arresters (524) frictionally engage serrated surface (528) to seize rotation of transducer housing (629) relative to body (18) for inhibiting rotation of transducer assembly (30).

F. Exemplary Translational Flat Clamp Lock

Figure 20:
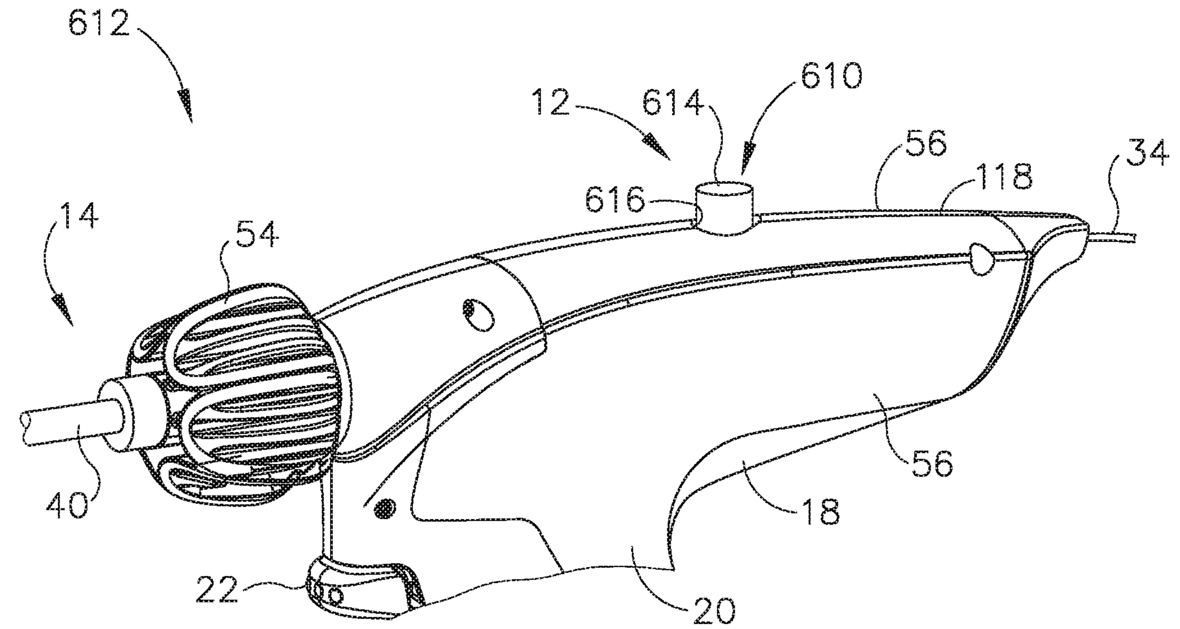
FIG. 20 depicts an enlarged perspective view of a sixth exemplary ultrasonic surgical instrument having a translational flat clamp lock.
Figure 21A:
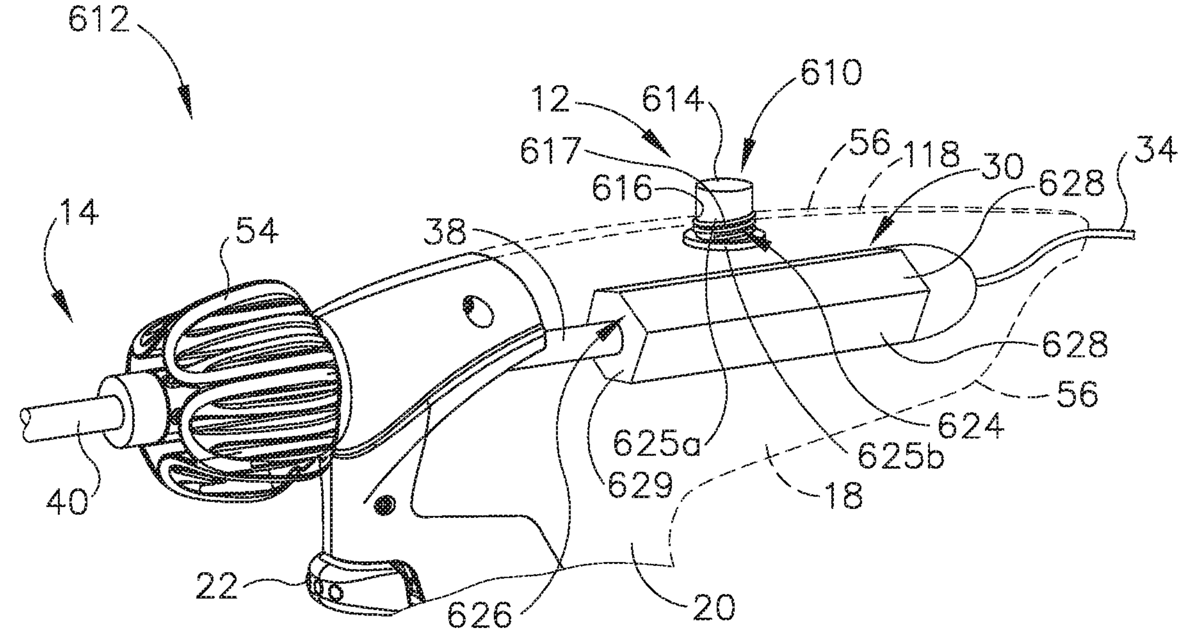
FIG. 21A depicts the enlarged perspective view of the ultrasonic surgical instrument of FIG. 20, but having various components removed for more clearly showing an ultrasonic transducer assembly and the translational flat clamp lock in an unlocked position.
Figure 21B:
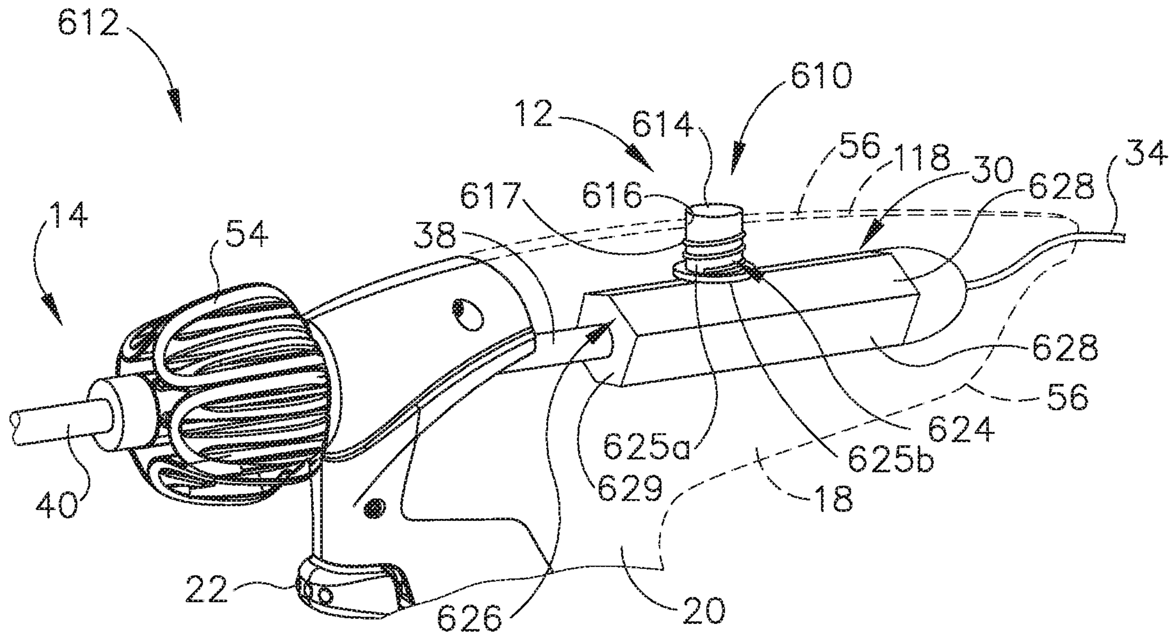
FIG. 21B depicts the enlarged perspective view of the ultrasonic surgical instrument of FIG. 20, but having various components removed for more clearly showing the ultrasonic transducer assembly and the translational flat clamp lock in a locked position.

FIGS. 20-21B illustrate a sixth exemplary transducer lock, in the form of a translational flat clamp lock (610) of a surgical instrument (612). Translational flat clamp lock (610) includes a lock switch (614) extending through a lock channel (616) in body (18). More particularly, lock channel (616) extends transversely through upper surface (118) of body (18) directly above the longitudinal axis. Lock switch (614) is thus translatable between an upper, unlocked position and a lower, locked position for respectively unlocking and locking rotation of transducer assembly (30) relative to body (18). In other words, lock switch (614) is configured to be directed inwardly toward the longitudinal axis from the unlocked position to the locked position. Given that lock switch (614) is generally depressed in use so as to be translate toward the longitudinal axis, lock switch (614) may also be referred to herein as a lock button. While lock switch (614) and lock channel (616) are positioned on upper surface (118) of body (18) of the present example, it will be appreciated that lock switch (614) and lock channel (616) may be alternatively positioned so as to cooperate with transducer assembly (30).

Lock switch (614) is resiliently mounted in lock channels (516) by a pair of biasing members (617), which urge lock switch (614) toward the unlocked position. The user may generally maintain depression of lock switch (614) to retain lock switches (614) in the locked position during coupling of waveguide (38) with transducer assembly (30). For example, the user may use one or more hands to selectively depress lock switch (614) toward the locked position as shown in FIG. 21B. Of course, alternative examples may use various detents or other structures for releasably securing the position of lock switch (614) as desired. The invention is thus not intended to be unnecessarily limited to either secured or biased lock switch (614) positions.

Translational flat clamp lock (610) further includes an arrester (624) operatively connected to lock switch (614) and an engagement feature (626) operatively connected to transducer assembly (30) that cooperate together to selectively allow or inhibit rotation of transducer assembly (30) relative to body (18). To this end, arrester (624) extends transversely inwardly from lock switch (614) toward the longitudinal axis and, in the unlocked position is transversely offset from engagement feature (626) and transducer assembly (30). By way of example, arrester (624) extends downwardly from lock switch (614) to a lower end portion (625*a*) having a flat (625*b*). Flat (625*b*) faces inwardly toward longitudinal axis for engagement with engagement feature (626) as shown in FIGS. 21A and 21B.

Engagement feature (626) of the present example includes a plurality of flats (628) extending along a transducer housing (629) of transducer assembly (30). More particularly, six flats (628) extend along transducer housing (629) such that a transverse cross-section of transducer housing (629) defines a hexagonal shape about the longitudinal axis. Each flat (628) extends in the longitudinal direction so as to be parallel with the longitudinal axis and, when rotated to the uppermost position about the longitudinal axis, is parallel with flat (625*b*) on lower end portion (625*a*) of arrester (624). Thus, regardless of the rotatable position of transducer housing (629) at least one flat (628) is positioned to receive flat (625*b*) of arrester thereagainst for engagement.

Engagement between flat (625*b*) and flat (628) tends to inhibit relative rotation. Moreover, increasing the transverse depression force on lock switch (614) in turn increases the compression force of flat (625*b*) against flat (628) of transducer housing (629). The user may thus apply more or less compression as desired for inhibiting rotation of transducer assembly (30). While the present example includes various flats (625*b*, 628) for inhibiting relative rotation, it will be appreciated that alternative cooperating surfaces may be so used. By way of further example, alternative structures extending respectively from arrester (624) and transducer housing (629) that cooperatively engage for inhibiting relative rotation may also be similarly configured. Accordingly, other structures for such engagement may be used with translational flat clamp lock (610), and the invention is not intended to be unnecessarily limited to the flats (625*b*, 628) described herein.

FIGS. 20 and 21A illustrate lock switches (614) in the upper, unlocked position with arrester (624) in an upper, disengaged position, which is offset from flat (628) of transducer housing (629). Transversely translating lock switch (614) downwardly from the unlocked position toward the locked position similarly translates arrester (624) downwardly from the disengaged position toward an engaged position shown in FIG. 21B. In the engaged position, flat (625*b*) of arrester (624) engages one of flats (628) to seize rotation of transducer housing (629) relative to body (18) for inhibiting rotation of transducer assembly (30).

G. Exemplary Pivot Flat Clamp Lock

Figure 22:
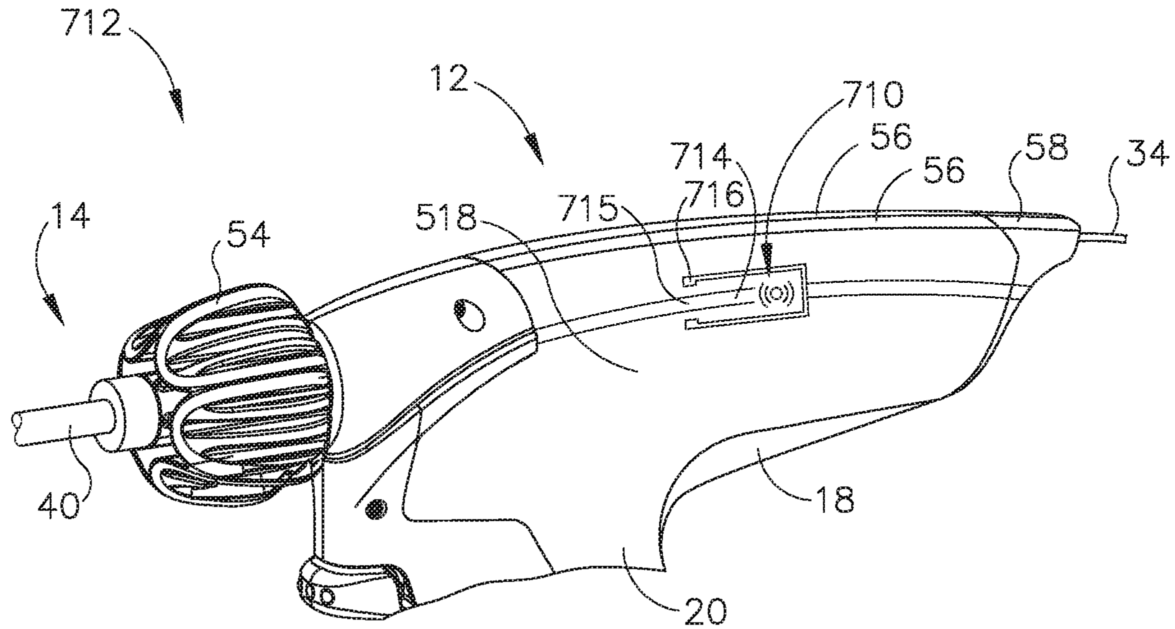
FIG. 22 depicts an enlarged perspective view of a seventh exemplary ultrasonic surgical instrument having a pivot flat clamp lock.
Figure 23A:
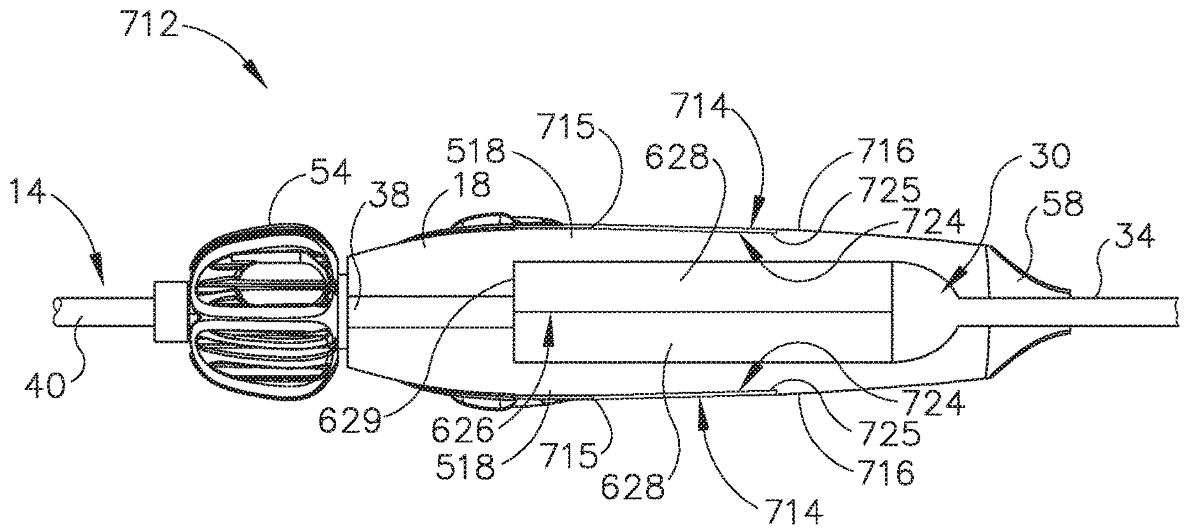
FIG. 23A depicts a top sectional view of the ultrasonic surgical instrument of FIG. 22, taken along a centerline of an ultrasonic transducer assembly, the pivot flat clamp lock being in an unlocked position.
Figure 23B:
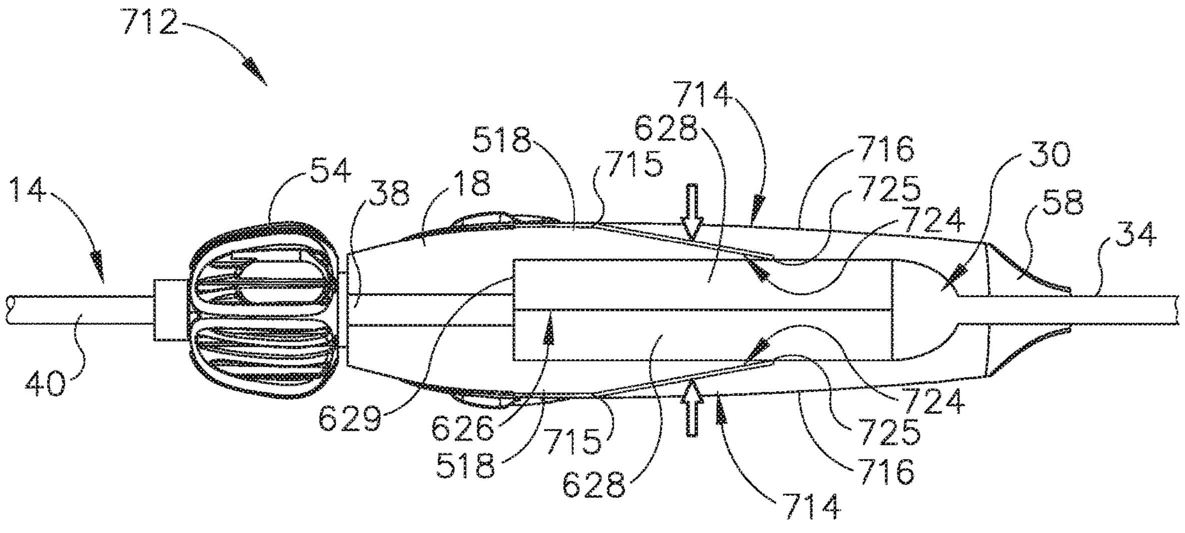
FIG. 23B depicts a top sectional view of the ultrasonic surgical instrument of FIG. 22, taken along a centerline of the ultrasonic transducer assembly, the pivot flat clamp lock being in a locked position.
Figure 24:
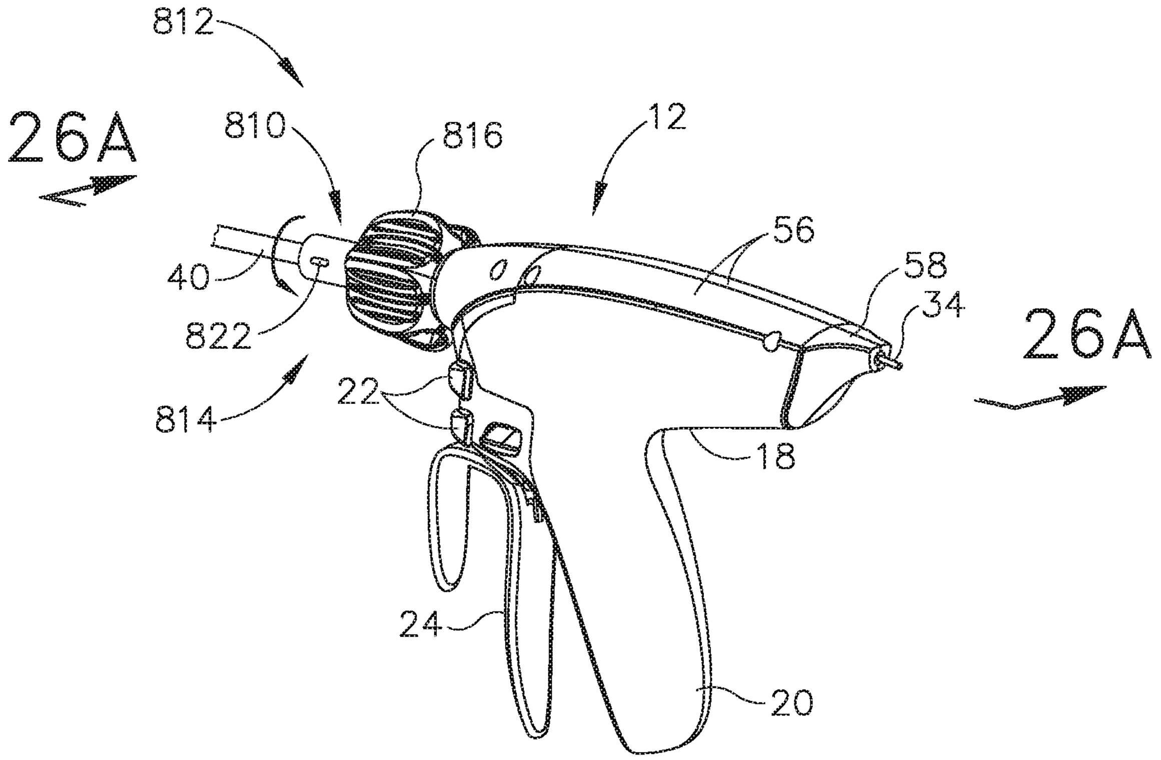
FIG. 24 depicts a perspective view of an eighth exemplary ultrasonic surgical instrument having a shaft assembly with an integral torque wrench.

FIGS. 22-23B illustrate a seventh exemplary transducer lock, in the form of a pivot flat clamp lock (710) of a surgical instrument (712). Pivot flat clamp lock (710) includes a pair of lock switches (714) extending respectively through a pair of lock channels (716) in body (18). More particularly, each lock switch (714) is a portion of body (18) having lock channel (716) generally surrounding lock switch (714), but connected to a remainder of body (18) by a living hinge (715). Each lock switch (714) is thus pivotable about living hinge (715) between an outer, unlocked position and an inner, locked position for respectively unlocking and locking rotation of transducer assembly (30) relative to body (18). In other words, each lock switch (714) is configured to be directed inwardly toward the longitudinal axis from the unlocked position to the locked position as shown in FIGS. 23A and 23B, respectively. Given that each lock switch (714) is generally depressed in use so as to be translate toward the longitudinal axis, lock switches (714) may also be referred to herein as lock buttons. While each lock switch (714) and lock channel (716) are positioned on side surfaces (518) of body (18) of the present example, it will be appreciated that lock switches (714) and lock channels (716) may be alternatively positioned so as to cooperate with transducer assembly (30). Furthermore, while the present example of pivot flat clamp lock (710) has two lock switches (714), it will be appreciated that fewer or more such switches (714) may be used in alternative examples. The invention is thus not intended to be unnecessarily limited to having two lock switches (714) and two lock channels (716) positioned as shown herein.

Each lock switch (714) is resiliently mounted in lock channels (716) via living hinge (715). The user may generally maintain depression of each lock switch (714) to retain lock switches (714) in the locked position during coupling of waveguide (38) with transducer assembly (30). For example, the user may use one or more hands to selectively squeeze lock switches (714) simultaneously toward the locked position. Of course, alternative examples may use various detents or other structures for releasably securing the position of lock switches (714) as desired. The invention is thus not intended to be unnecessarily limited to either secured or biased lock switch (714) positions.

Pivot flat clamp lock (710) further includes an arrester (724) operatively connected to lock switch (714) and the plurality of flats (628) along transducer housing (629) that cooperate together to selectively allow or inhibit rotation of transducer assembly (30) relative to body (18). To this end, each arrester (724) includes an inner flat (725) of lock switch (714) that extends transversely along an interior of each respective lock switch (714) and, in the unlocked position, is laterally offset from flats (628) of transducer housing (629). Flat (725) faces inwardly toward the longitudinal axis for engagement with flats (628) as shown in FIGS. 23A and 23B.

Engagement between flats (725) and flats (628) tends to inhibit relative rotation. Moreover, increasing the lateral depression force on lock switches (714) in turn increases the compression force of flats (725) against flats (628) of transducer housing (629). The user may thus apply more or less compression as desired for inhibiting rotation of transducer assembly (30). While the present example includes various flats (725, 628) for inhibiting relative rotation, it will be appreciated that alternative cooperating surfaces may be so used. By way of further example, alternative structures extending respectively from arrester (724) and transducer housing (629) that cooperatively engage for inhibiting relative rotation may also be similarly configured. Accordingly, other structures for such engagement may be used with pivot flat clamp lock (710), and the invention is not intended to be unnecessarily limited to the flats (725, 628) described herein.

FIGS. 22 and 23A illustrate lock switches (714) in the laterally outward, unlocked position with arrester (524) in a laterally outward, disengaged position, which is offset from flats (628) of transducer housing (629). Laterally pivoting lock switches (714) inwardly from the unlocked position toward the locked position similarly pivots arrester (724) inward from the disengaged position toward an engaged position shown in FIG. 23B. In the engaged position, flats (725) of arresters (724) engage respective flats (628) to seize rotation of transducer housing (629) relative to body (18) for inhibiting rotation of transducer assembly (30).

III. EXEMPLARY INTEGRAL TORQUE WRENCH

In the examples described above with respect to FIGS. 1-23B, waveguide (38) is rotatably coupled with transducer assembly (30) to the predetermined torque with torque wrench (60) for each of surgical instruments (10, 112, 212, 312, 412, 512, 612, 712). In each instance, torque wrench (60) is separable from surgical instruments (10, 112, 212, 312, 412, 512, 612, 712), such that torque wrench (60) is applied to shaft assembly (14) for coupling waveguide (38) to transducer assembly (30) and then removed from shaft assembly (14) following tightening of waveguide (38) to the predetermined torque so that each surgical instrument (10, 112, 212, 312, 412, 512, 612, 712) may then be used to perform the surgical procedure. However, handling and manipulating torque wrench (60) separately from surgical instruments (10, 112, 212, 312, 412, 512, 612, 712) may add further complexity to the surgical procedure and may be difficult to manage in some instances.

It may thus be desirable to incorporate an alternative torque wrench into one or more portions of surgical instruments (10, 112, 212, 312, 412, 512, 612, 712) that remains with surgical instruments (10, 112, 212, 312, 412, 512, 612, 712) during use, rather than being applied and removed in advance of use. An example of such an integral torque wrench (810) is incorporated into a surgical instrument (812) described below in additional detail and illustrated in FIGS. 24-26B. Integral torque wrench (810) is incorporated into a shaft assembly (814) and remains connected with knob (816) prior to coupling waveguide (38) with transducer assembly (30) and after coupling waveguide (38) with transducer assembly (30). Integral torque wrench (810) may thus be manipulated as desired for coupling waveguide (38) with transducer assembly (30) at the predetermined torque while also allowing for manipulation of shaft assembly (814) as described above with respect to shaft assembly (14). While integral torque wrench (810) is shown incorporated into shaft assembly (814) and connected to knob (816), it will be appreciated that alternative arrangements for limiting torque to waveguide (38) may also be provided. The invention is thus not intended to be unnecessarily limited to the specific arrangement of integral torque wrench (810) with knob (816) as shown herein. Furthermore, like numbers provided below indicate like features described above in additional detail. It should also be understood that integral torque wrench (810) may be used in combination with any of the transducer assembly (30) arresting components described above. In other words, integral torque wrench (810) may be readily incorporated into any of surgical instruments (10, 112, 212, 312, 412, 512, 612, 712) described above.

As seen in FIGS. 24-26B, surgical instrument (812) has shaft assembly (814) with integral torque wrench (810) connected to knob (816). Integral torque wrench (810) receives outer tube (40) through a bore (818) and is selectively rotatable about the longitudinal axis on outer tube (40). Integral torque wrench (810) releasably connects to knob (816) to transmit torque from integral torque wrench (810) to knob (816) via a releasable coupling (820). Releasable coupling (820) transmits torque in a rotatable, tightening direction up to the predetermined torque at which waveguide (38) operatively couples with transducer assembly (30). However, in order to inhibit overtightening of waveguide (38) with transducer assembly (30), releasable coupling (820) is configured to release knob (816) as the transmitted torque exceeds the predetermined torque. Thereby, integral torque wrench (810) rotatably slips relative to knob (816) for inhibiting overtightening of waveguide (38) (see FIG. 26A) with transducer assembly (30). It should also be understood that torque wrench (810) may emit audible and/or tactile “clicks” when torque wrench (810) rotatably slips relative to knob (816).

Figure 25:
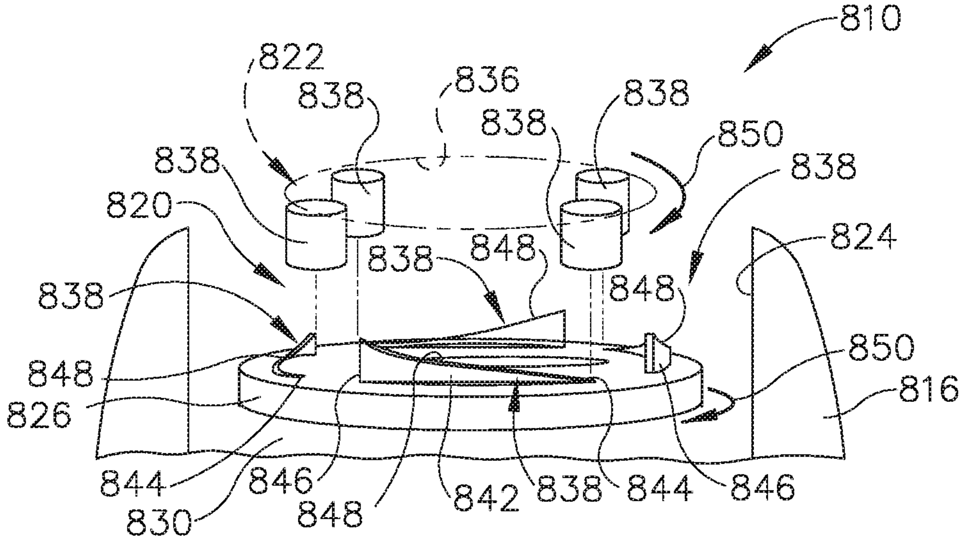
FIG. 25 depicts an enlarged, partially exploded perspective view of the shaft assembly of FIG. 24 having various components removed for more clearly showing various features of the integral torque wrench.
Figure 26A:
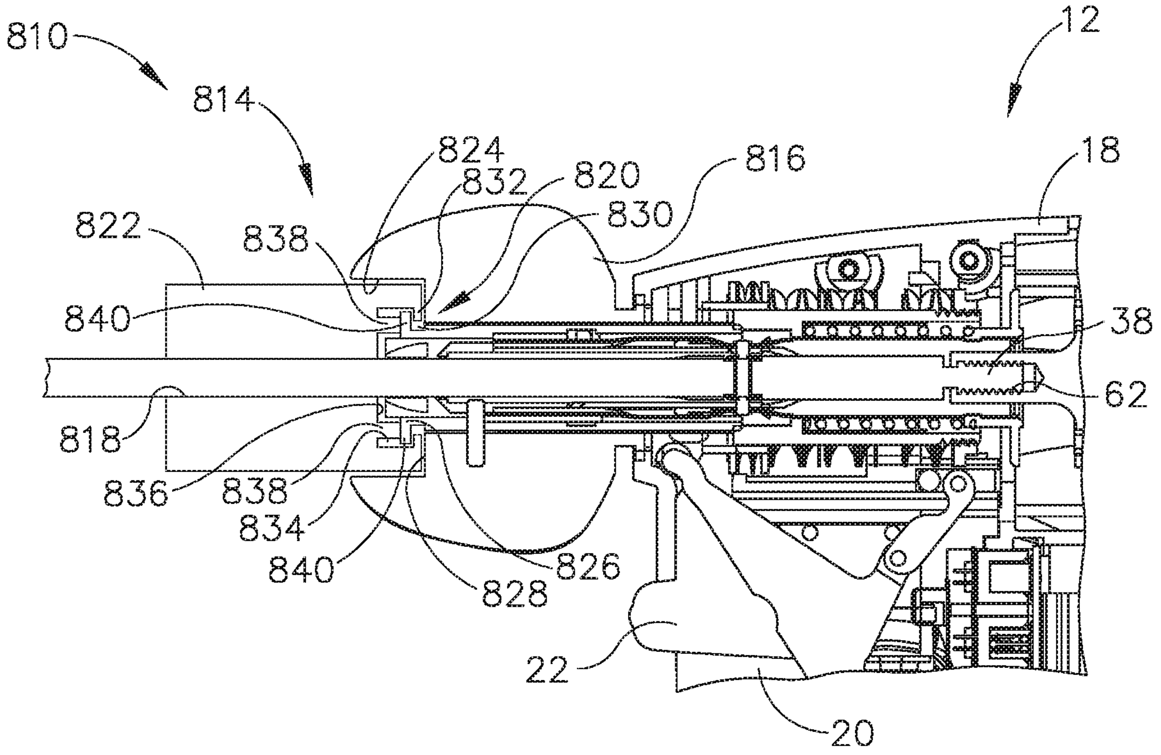
FIG. 26A depicts an enlarged cross-sectional view of the ultrasonic surgical instrument of FIG. 24, taken along section line 26A-26A of FIG. 24, showing the integral torque wrench rotatably engaged with a remainder of the shaft assembly.

As seen in FIGS. 25-26A, integral torque wrench (810) includes a cylindrical body (822) extending coaxially along the longitudinal axis, such that cylindrical body (822) is positioned concentrically about the longitudinal axis. A proximal end portion of cylindrical body (822) includes a portion of releasable coupling (820), whereas a distal end portion of knob (816) includes a remaining portion of releasable coupling (820). These opposing portions of releasable coupling (820) cooperatively engage such that rotating integral torque wrench (810) simultaneously rotates knob (816) and cooperatively disengages to allow for relative slip for limiting torque transferred therebetween.

The proximal end portion of cylindrical body (822) is axially fixed to the distal end portion of knob (816) while allowing cylindrical body (822) to rotate relative to knob (816) during slip. More particularly, the distal end of knob (816) includes a cylindrical distal opening (824) extending coaxially along the longitudinal axis that rotatably receives the proximal end portion of cylindrical body (822). An annular pedestal (826) extends distally toward cylindrical body (822) from an inner face (828) of knob (816) to define an annular securement channel (830) therebetween. An annular securement lip (832) extends radially inwardly from the proximal end portion of cylindrical body (822) and is configured to be received within annular securement channel (830) to axially fix integral torque wrench (810) to knob (816). Each of annular pedestal (826), annular securement channel (830), and annular securement lip (832) is coaxial with each other and the longitudinal axis. Annular securement lip (832) of integral torque wrench (810) is thus captured in the longitudinal direction within annular securement channel (830) between annular pedestal (826) and inner face (828), but configured for relative rotation in securement channel (830) during slip as discussed below in greater detail.

Annular securement lip (832) surrounds a cylindrical proximal opening (834) into cylindrical body (822) that also extends distally and coaxially along the longitudinal axis. Proximal opening (834) into cylindrical body (822) receives annular pedestal (826) for cooperative engagement and disengagement therebetween. To this end, with particular reference to FIG. 25, an inner face (836) of cylindrical body (822) has at least one compressible member (838) extending proximally toward annular pedestal (826). Similarly, annular pedestal (826) has at least one cam (840) extending distally toward inner face (836) for engagement with compressible member (838). In the present example, inner face (836) and annular pedestal (826) respectively have four such compressible members (838) and four such cams (840). Compressible members (838) and cams (840) are positioned angularly about inner face (836) and annular pedestal (826), respectively, and positioned such that each compressible member (838) cooperates with one respective cam (840). Each cam (840) more particularly includes a cam ramp (842) that extends along a radial arc about the longitudinal axis from an initial end (844) to a terminal end (846). A ramp surface (848) of cam ramp (842) at initial end (844) is essentially flush with a distal surface of annular pedestal (826), but projects distally away from the distal surface of annular pedestal (826) toward terminal end (846). In other words, a longitudinal depth of cam ramp (842) increases from initial end (844) to terminal end (846).

Compressible member (838) is generally configured to compress in a distal direction from an elongated state to a compressed state and resiliently return from the compressed state to the elongated state. In the elongated state, compressible member (838) initially compresses in the distal direction with the application of a relatively small distal force. However, as compressible member (838) compresses toward the compressed state, the applied distal force increases to cause similar compression. In other words, as compression increases, the amount of applied distal force must also increase to continue further compression.

Each compressible member (838) is generally engaged with annular pedestal (826), because cylindrical body (822) is axially fixed relative to knob (816) as discussed above. At a minimum torque, each compressible member (838) frictionally engages initial end (844) of ramp surface (848) as shown in FIGS. 25 and 26A in the elongated state. Selectively rotating cylindrical body (822) in a tightening direction (850) similarly rotates each compressible member (838) about the longitudinal axis. In turn, the collective frictional engagement between compressible members (838) and ramp surfaces (848) causes annular pedestal (826) and knob (816) to also rotate in tightening direction (850). Such minimum torque may be sufficient for threading an initial portion of waveguide (38) into transducer assembly (30).

Figure 26B:
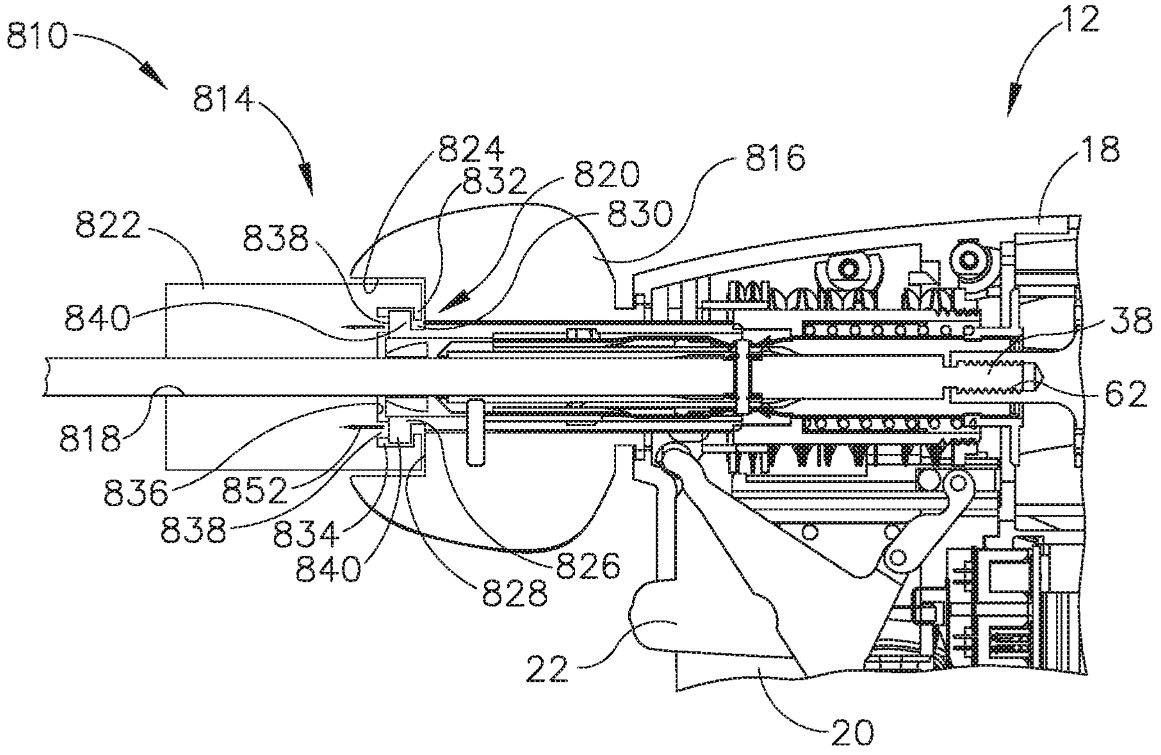
FIG. 26B depicts an enlarged cross-sectional view of the ultrasonic surgical instrument of FIG. 24, taken along section line 26A-26A of FIG. 24, showing the integral torque wrench slipping relative to the remainder of the shaft assembly.

Once the amount of torque required to continue threading waveguide (38) into transducer assembly (30) increases beyond this minimum torque, the compressible member (838) reactively compresses against ramp surface (848) as cam ramp (842) begins to rotatably slip past compressible member (838). Resilient compression increases frictional engagement between compressible member (838) and ramp surface (848) and increases the amount of torque transmission capable in the tightening direction between cylindrical body (822) and knob (816). As the amount of tightening torque required to rotate waveguide (38) into transducer assembly (30) increases, cam ramp (842) will continually slip past compressible member (838) to further compress compressible member in the distal direction toward the compressed state for additional frictional engagement until reaching terminal end (846) of cam ramp (842). By way of example, FIG. 26B shows compressible member being compressed in the distal direction, as indicated by arrow (852), while being rotated in tightening direction (850). As is further shown in FIG. 26B, annular pedestal (826) is effectively in compression between compressible members (838) and annular securement lip (832) as torque increases toward the predetermined torque for operatively coupling waveguide (38) with transducer assembly (30).

Once each compressible member (838) is resiliently compressed to the compressed state at the respective terminal end (846) of cam ramp (848), integral torque wrench (810) is configured to apply torque at the predetermined torque to complete the coupling of waveguide (38) to transducer assembly (30). Just as the coupling torque between waveguide (38) and transducer assembly (30) increases beyond the predetermined torque, cam ramps (838) further slip relative to compressible members (838). Thus, each compressible member (838) slips off of terminal end (846) of cam ramp (842) and lands adjacent to another initial end (844) of a neighboring cam ramp (842) to limit the application of additional torque beyond the predetermined torque. Further rotation of integral torque wrench (810) in tightening direction (850) is possible by the user, but, since frictional engagement between compressible members (838) and cam ramps (842) is limited to the predetermined torque transmission, further rotation will simply result in continual slip between integral torque wrench (810) and knob (816). By way of further example, slippage of compressible member (838) relative to cam ramp (842) may also generate an audible indicator (e.g., a "click"), a tactile indicator, or other signal to the user that waveguide (38) is coupled with transducer assembly (30) at the predetermined torque. Integral torque wrench (810) may thus also be one example of an integral torque indicator.

The present example of integral torque wrench (810) provides various releasable coupling features on each of cylindrical body (822) and knob (816). It will be appreciated that alternative arrangements of the coupling features on cylindrical body (822) and/or knob (816) may be possible in accordance with the invention. For example, compressible members (838) and cams (840) may be positioned on either one of cylindrical body (822) and knob (816) for respective cooperation as discussed herein. Similarly, alternative compressible members and cams for guiding compression and frictional engagement may be used. The invention is thus not intended to be unnecessarily limited to the particular compressible members (838) and cams (840) described herein.

IV. EXEMPLARY INTEGRAL TORQUE INDICATOR

While limiting torque to the predetermined torque for operatively coupling waveguide (38) with transducer assembly (30) reduces the likelihood of overtightening waveguide (38), the user selectively rotating waveguide (38) may still not appreciate when operative coupling between waveguide (38) with transducer assembly (30) is complete. On one hand, if the user continues to rotate waveguide (38) after operative coupling, the user is needlessly extending the time for installation. On the other hand, if the user prematurely stops rotation by inadvertently misjudging the operative coupling, waveguide (38) and transducer assembly (30) may function improperly. At best, these decisions may extend surgical procedure. At worst, these decisions may damage any one of surgical instruments (10, 112, 212, 312, 412, 512, 612, 712, 812) and/or reduce the likelihood of a positive outcome for the patient.

It may thus be desirable to incorporate an integral torque indicator into one or more portions of surgical instruments (10, 112, 212, 312, 412, 512, 612, 712, 812) for communicating a signal to the user that waveguide (38) has been coupled with transducer assembly (30) at the predetermined torque. One such integral torque indicator (910) is incorporated into a surgical instrument (912) described below in additional detail and illustrated in FIGS. 27-31. In the present example, portions of integral torque indicator (910) are incorporated into a shaft assembly (914) and a transducer assembly (926). However, it will be appreciated that such portions may be alternatively positioned so as to cooperate together to generate the signal. The invention is thus not intended to be unnecessarily limited to the specific arrangement of integral torque indicator (910) as shown herein. Furthermore, like numbers provided below indicate like features described above in additional detail.

Figure 27:
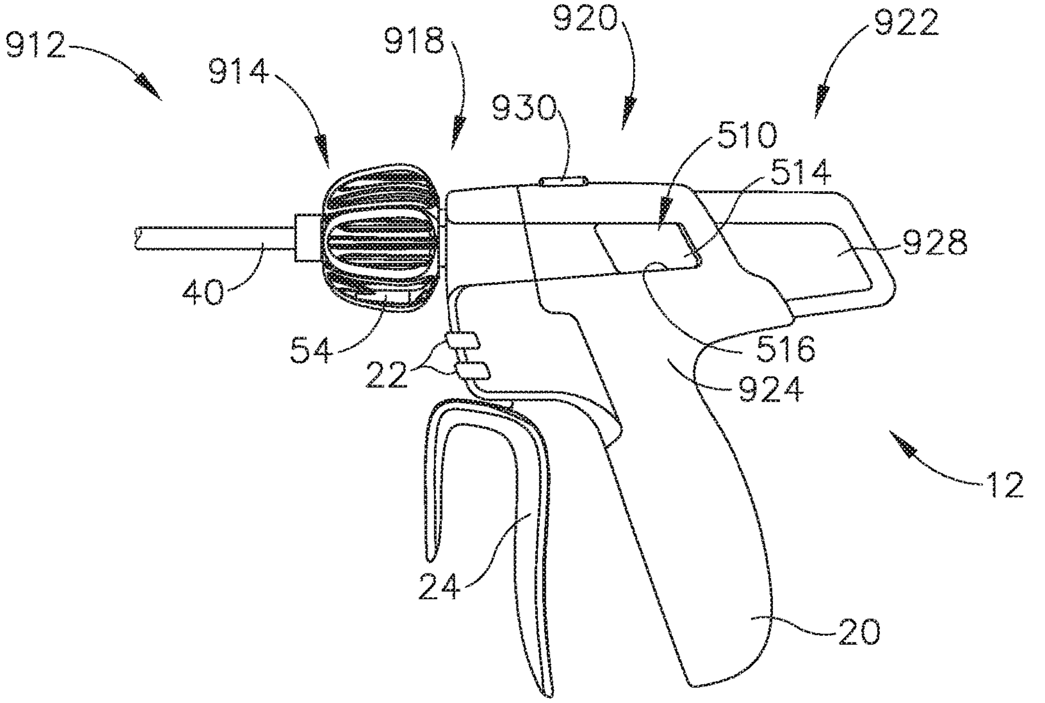
FIG. 27 depicts a side elevational view of a ninth exemplary ultrasonic surgical instrument.
Figure 28:
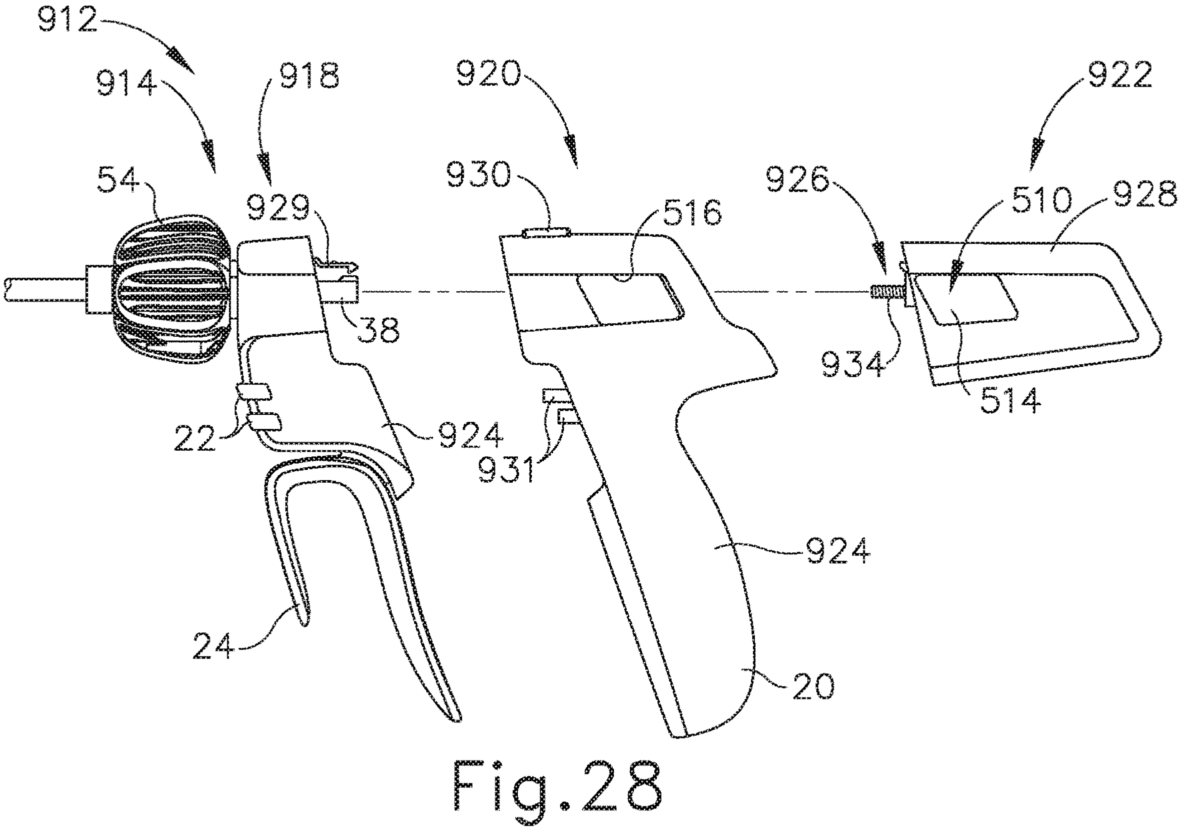
FIG. 28 depicts a partially exploded side elevational view of the ultrasonic surgical instrument of FIG. 27.
Figure 29:
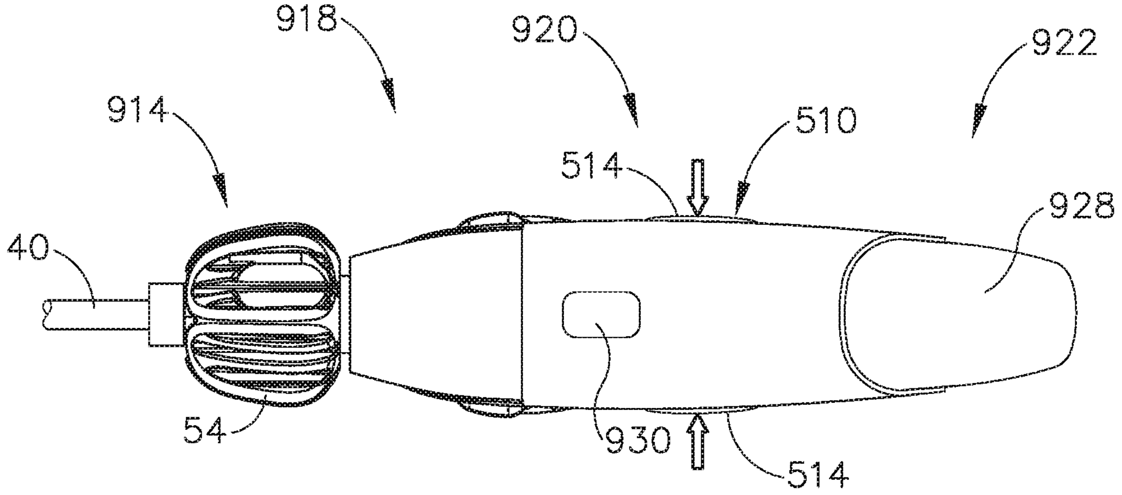
FIG. 29 depicts a top view of a handle assembly of the ultrasonic surgical instrument of FIG. 27 with a transducer lock in a locked position.

As seen in FIGS. 27-29, surgical instrument (912) includes a distal portion (918), an intermediate portion (920), and a proximal portion (922). Distal portion (918) has shaft assembly (914) with knob (54) and waveguide (38), end effector (16) (see FIG. 1), buttons (22), trigger (24) and a portion of a body (924). Intermediate portion (920) has another portion of body (924) with pistol grip (20). Proximal portion (922) generally includes transducer assembly (926) contained with a cover (928) for storage and protection. Accordingly, cover (928) may also be considered a remaining portion of body (924) of surgical instrument (912). One or more of distal, intermediate, and proximal portions (918, 920, 922) of surgical instrument (912) may be disposable and/or reusable as discussed above with respect to surgical instrument (10) (see FIG. 1). In the present example, distal portion (918) is disposable, whereas intermediate and proximal portions (920, 922) are reusable. By way of further example, distal portion (918) also includes a keyed clip member (929) configured to be received within an alignment hole (not shown) in intermediate portion (920). Intermediate portion (920) includes a release switch (930) that releasably connects with keyed clip member (929) for at least partially mechanically coupling distal and intermediate portions of body (18). Intermediate portion (920) of body (18) further includes an electrical connector (931) received within distal portion (918) of body (18) for electrically coupling intermediate and distal portions (920, 918) of surgical instrument (912).

Proximal portion (922) of surgical instrument (912) includes grip clamp lock (510) having lock switch (514) extending through cover (928) for seizing rotation of transducer assembly (926) relative to cover (928). Body (18) of intermediate portion (920) also includes a pair of additional lock channels (516) configured to respectively receive lock switches (514) as transducer assembly (926) is removably received within intermediate portion (920) of body (18). The user may thus access lock switch (514) and squeeze lock switches (514) as shown in FIG. 29 for inhibiting rotation of transducer assembly (926) during coupling of waveguide (38) with transducer assembly (926) as discussed above.

Figure 30A:
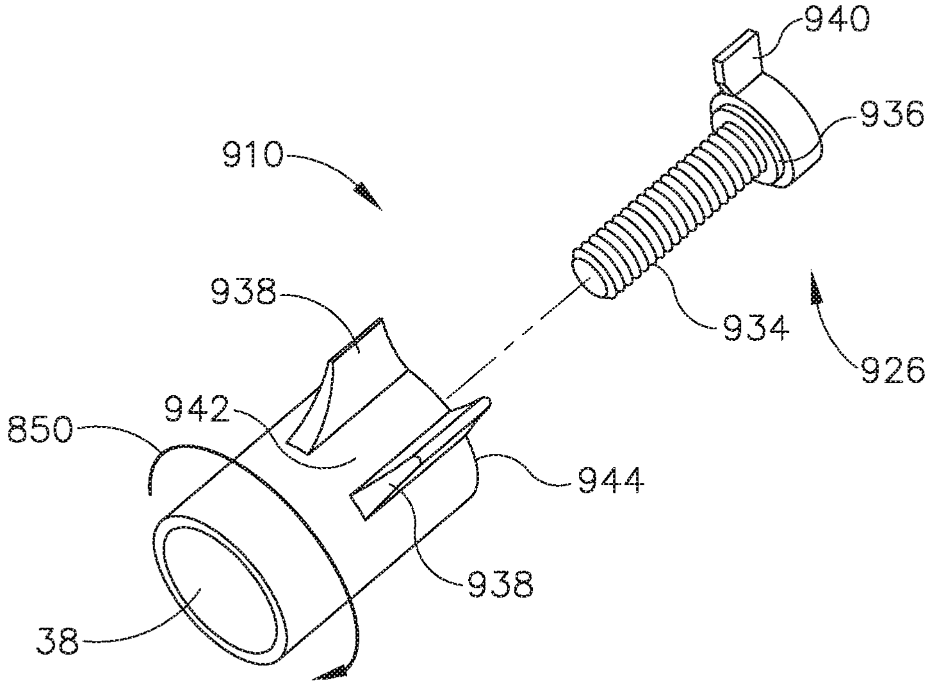
FIG. 30A depicts an enlarged perspective view of an integral torque indicator of the ultrasonic surgical instrument of FIG. 27.
Figure 30C:
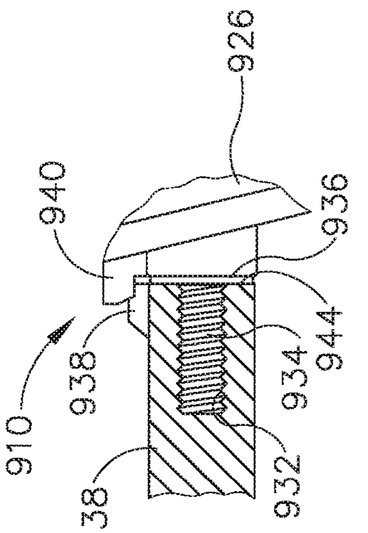
FIG. 30C depicts a side elevational view of the acoustic waveguide of the ultrasonic surgical instrument of FIG. 27 being coupled with the ultrasonic transducer assembly of the ultrasonic surgical instrument of FIG. 27, with the integral torque indicator of FIG. 30A generating an audible sound for indicating a predetermined coupling torque between the acoustic waveguide and the ultrasonic transducer assembly.
Figure 30B:
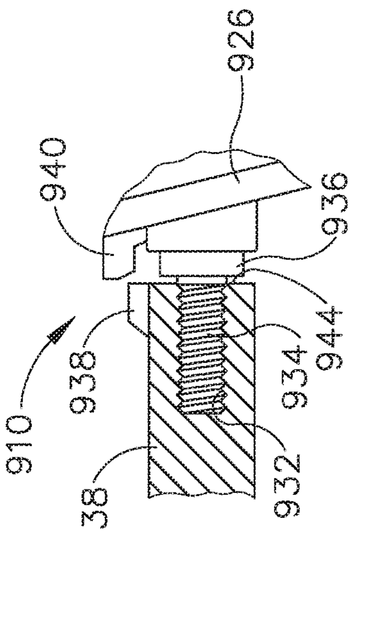
FIG. 30B depicts a side elevational view of an acoustic waveguide of the ultrasonic surgical instrument of FIG. 27 being coupled with an ultrasonic transducer assembly of the ultrasonic surgical instrument of FIG. 27.

FIGS. 30A-30C show integral torque indicator (910) communicating the audible and tactile signal upon coupling waveguide (38) with transducer assembly (926). In the present example, waveguide (38) has a threaded hole (932) coaxially positioned within waveguide (38), whereas transducer assembly (926) has a threaded stud (934) configured to be threadably received within threaded hole (932) for coupling. Transducer assembly (926) further includes a resilient stop, such as a resilient o-ring (936), which is positioned about a proximal end of threaded stud (934) against transducer assembly (926). Resilient o-ring is configured to provide additional resilience within the threaded joint of threaded hole (932) and threaded stud (934) at the predetermined torque for inhibiting waveguide (38) from inadvertently loosening during use.

Integral torque indicator (910) includes a pair of offset fin members (938) configured to cooperatively engage a pick tab (940) for generating the audible and tactile signal. More particularly, fin members (938) extend radially from a proximal portion of waveguide (38) and are positioned angularly relative to each other to define a space (942) therebetween. Each fin member (938) is adjacent to a proximal face (944) of waveguide (38) for engagement with pick tab (940) during coupling of waveguide (38) with threaded stud (934). Pick tab (940) longitudinally extends from transducer assembly (926) above the longitudinal axis and over o-ring (935) in the distal direction. Pick tab (940) is generally rigid, whereas fin members (938) are relatively resilient and configured to audibly and tactilely resonate when plucked.

In use, with grip clamp lock (510) having lock switches (514) in the locked positions, the user rotates waveguide (38) in tightening direction (850). Threaded hole (932) rotatably receives threaded stud (934) such that waveguide (38) is threaded onto threaded stud as shown in FIGS. 30A and 30B. Proximal face (944) engages o-ring (936) and compresses o-ring (936) against transducer assembly (926). In turn, the torque applied to couple waveguide (38) with transducer assembly (926) increases toward the predetermined torque.

Figure 31:
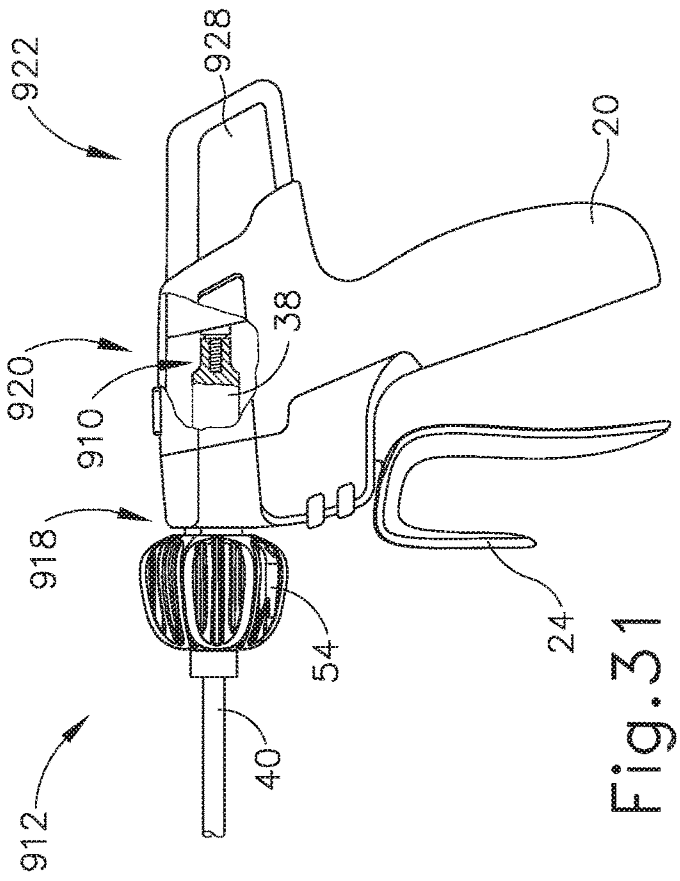
FIG. 31 depicts a side elevational view of a handle assembly of the ultrasonic surgical instrument of FIG. 27 having various components removed for clarity and another transducer lock in an unlocked position.

Throughout coupling of waveguide (38) and transducer assembly (926), fin members (938) rotate about the longitudinal axis while being drawn proximally toward pick tab (940). Fin members (938) and pick tab (940) are positioned relative to each other such that as the torque reaches the predetermined torque shown in FIG. 30C, pick tab (940) sequentially plucks fin members (938). The second pluck of fin members (938) generates the second signal to effectively communicate to the user that the waveguide (38) and transducer assembly (926) are operatively coupled with the predetermined torque as shown in FIG. 31. Of course, any number of signals may be tuned to the predetermined torque and the invention is not intended to be unnecessarily limited to two such signals. It will be further appreciated that any such signal, audible and/or tactile may be so used, and the invention is not intended to be unnecessarily limited to the particular signals described herein.

V. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an instrument body; (b) an ultrasonic transducer assembly rotatably mounted along a longitudinal axis within the instrument body; and (c) a transducer lock having a lock member configured to be selectively moved between an unlocked position to a locked position, wherein the ultrasonic transducer assembly is configured to be selectively rotated about the longitudinal axis relative to the instrument body with the lock member in the unlocked position, and wherein the transducer lock is configured to seize the ultrasonic transducer assembly with the lock member in the locked position to thereby selectively inhibit rotation about the longitudinal axis relative to the housing for rotatably coupling with an acoustic waveguide.

Example 2

The surgical instrument of Example 1, wherein the instrument body includes a switch channel, wherein the lock member includes a lock switch movably mounted in the lock channel, and wherein the lock switch is configured to be manipulated by a user between the locked and unlocked positions.

Example 3

The surgical instrument of Example 2, wherein the transducer lock further includes an arrester and an engagement feature, wherein the arrester is operatively connected to the lock switch and configured to selectively move between a disengaged position and an engaged position as the lock switch is respectively moved between the unlocked position and the locked position, wherein the engagement feature is connected to the ultrasonic transducer assembly and configured to be engaged by the arrester in the engaged position such that the engagement feature and the arrester cooperatively inhibit rotation of the ultrasonic transducer assembly about the longitudinal axis.

Example 4

The surgical instrument of Example 3, wherein the engagement feature includes an engagement collar connected to the ultrasonic transducer assembly and positioned concentrically about the longitudinal axis, wherein the engagement collar has a plurality of teeth positioned angularly about the engagement collar, and wherein the arrester is configured to be received between the plurality of teeth in the engaged position to rotatably engage the engagement collar thereby inhibiting rotation of the engagement collar and the ultrasonic transducer assembly connected thereto.

Example 5

The surgical instrument of Example 4, wherein at least a portion of the switch channel extends in a longitudinal direction along the instrument body, and wherein the lock switch is configured to selectively translate along the longitudinal direction between the unlocked position and the locked position to selectively translate the arrester between the disengaged position and the engaged position.

Example 6

The surgical instrument of Example 4, wherein the lock switch is configured to selectively translate along a transverse direction between the unlocked position and the locked position to selectively translate the arrester between the disengaged position and the engaged position.

Example 7

The surgical instrument of Example 4, wherein the arrester includes an annular body having at least one arrest member projecting radially therefrom configured to be received between the plurality of teeth, wherein the annular body is positioned concentrically about the longitudinal axis, and wherein the lock switch is configured to selectively translate along the longitudinal direction between the unlocked position and the locked position to selectively translate the arrester between the disengaged position and the engaged position.

Example 8

The surgical instrument of Example 7, wherein the lock switch is further configured to selectively rotate about the longitudinal axis between the unlocked position and the locked position to selectively rotate the arrester between the disengaged position and the engaged position.

Example 9

The surgical instrument of Example 4, wherein the lock switch is configured to selectively pivot along a transverse direction between the unlocked position and the locked position to selectively pivot the arrester between the disengaged position and the engaged position.

Example 10

The surgical instrument of Example 3, wherein the ultrasonic transducer assembly includes a transducer housing and the engagement feature is positioned on the transducer housing, wherein the lock switch is configured to move toward the longitudinal axis from the unlocked position toward the locked position, and wherein the arrester extends from the lock switch toward the engagement feature on the transducer housing such that the lock switch is movable toward the longitudinal axis to thereby move the arrester toward the engagement feature.

Example 11

The surgical instrument of Example 10, wherein arrester is configured to frictionally engage the engagement feature on the transducer housing in the engaged position to thereby inhibit rotation of the ultrasonic transducer assembly.

Example 12

The surgical instrument of Example, 10, wherein the engagement feature comprises at least one flat extending along the transducer housing, and the lock switch and arrester are configured to be selectively moved toward the longitudinal axis such that the arrester engages the at least one flat to thereby inhibit rotation of the ultrasonic transducer assembly.

Example 13

The surgical instrument of Example 1, wherein the lock member is biased toward the unlocked position.

Example 14

The surgical instrument of Example 1, further comprising a torque wrench configured to connect to a shaft assembly for coupling the acoustic waveguide to the ultrasonic transducer assembly with a predetermined torque.

Example 15

The surgical instrument of Example 1, further comprising a torque indicator configured to generate a signal to a user that the acoustic waveguide is coupled with the ultrasonic transducer assembly with a predetermined amount of torque.

Example 16

A surgical instrument, comprising: (a) an end effector; (b) a shaft assembly extending proximally from the end effector along a longitudinal axis, wherein the shaft assembly includes: (i) an acoustic waveguide extending along the longitudinal axis; (ii) a knob operatively connected to the acoustic waveguide, wherein the knob is configured to be selectively rotated and thereby rotate the acoustic waveguide; and (c) an integral torque wrench positioned internally to the knob and connected to the knob via a releasable coupling such that the integral torque wrench is configured to rotate with the knob, wherein the releasable coupling is configured to transmit torque from the integral torque wrench to the knob up to a predetermined torque, and wherein the releasable coupling is configured to release the knob as the transmitted torque exceeds the predetermined torque such that the integral torque wrench rotatably slips relative to the knob for inhibiting the transmission of torque through the knob from exceeding the predetermined torque while coupling the acoustic waveguide to an ultrasonic transducer assembly.

Example 17

The surgical instrument of Example 16, further comprising: (a) an instrument body; and (b) an ultrasonic transducer assembly rotatably mounted within the instrument body such that the ultrasonic transducer assembly is configured to selectively rotate about the longitudinal axis, wherein the ultrasonic transducer assembly is configured to rotatably couple with the acoustic waveguide.

Example 18

The surgical instrument of Example 16, wherein the integral torque wrench extends concentrically along the longitudinal axis and is configured to rotate about the longitudinal axis.

Example 19

The surgical instrument of Example 18, wherein the integral torque wrench comprises: (i) a body, (ii) a compressible member, and (iii) a cam, wherein one of the compressible member and the cam extend from the body and the other of the compressible member and the cam extend from the knob, wherein compressible member is engaged with the cam to transmit torque therethrough, wherein the cam is configured to compress the compressible member as the torque being transmitted therethrough is increased, and wherein the compressible member is configured to slip from the cam to disengage the compressible member from the cam as the torque being transmitted therethrough exceeds the predetermined torque.

Example 20

A surgical instrument, comprising: (a) an instrument body; (b) an ultrasonic transducer assembly rotatably mounted along a longitudinal axis within the instrument body such that the ultrasonic transducer assembly is configured to selectively rotate about the longitudinal axis; (c) an acoustic waveguide configured to threadably couple with the ultrasonic transducer assembly; and (d) an integral torque indicator, including: (i) a first member extending from the acoustic waveguide, and (ii) a second member extending from the ultrasonic transducer assembly, wherein the first and second members are positioned such that the first member is configured to engage the second member as the acoustic waveguide is threadably coupled with the ultrasonic transducer assembly with a predetermined amount of torque, and wherein the first and second members are configured to engage each other to thereby generate a signal indicative of the predetermined amount of torque for a user.

VI. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:

(a) an end effector;

(b) a shaft assembly extending proximally from the end effector along a longitudinal axis, wherein the shaft assembly includes:

(i) an acoustic waveguide extending along the longitudinal axis;

(ii) a knob operatively connected to the acoustic waveguide, wherein the knob is configured to be selectively rotated and thereby rotate the acoustic waveguide; and (c) an integral torque wrench, including:

(i) a wrench body positioned between the knob and the end effector, and (ii) a releasable coupling connecting the wrench body to the knob such that the wrench body is configured to rotate with the knob and transmit torque from the wrench body to the knob up to a predetermined torque, wherein the releasable coupling is configured to rotatably release the knob from the wrench body as the transmitted torque exceeds the predetermined torque such that the wrench body rotatably slips relative to the knob for inhibiting the transmission of torque therethrough, wherein the releasable coupling includes a compressible member and a cam, wherein one of the compressible member and the cam extend from the wrench body and the other of the compressible member and the cam extend from the knob, wherein the compressible member is engaged with the cam to transmit torque therethrough, wherein the cam is configured to compress the compressible member as the torque being transmitted therethrough is increased, and wherein the compressible member is configured to slip from the cam to disengage the compressible member from the cam as the torque being transmitted therethrough exceeds the predetermined torque.

2. The surgical instrument of claim 1, wherein the releasable coupling includes a body portion positioned on the wrench body and a knob portion positioned on the knob.

3. The surgical instrument of claim 2, wherein at least a portion of the knob portion of the releasable coupling is positioned within the knob.

4. The surgical instrument of claim 2, wherein the body portion of the releasable coupling is configured to deflect relative to the knob portion of the releasable coupling as the transmitted torque exceeds the predetermined torque such that the body portion rotatably slips relative to the knob portion for inhibiting the transmission of torque through the releasable coupling.

5. The surgical instrument of claim 4, wherein the body portion of the releasable coupling is configured to proximally deflect or distally deflect relative to the knob portion.

6. The surgical instrument of claim 4, wherein the body portion of the releasable coupling is configured to resiliently deflect relative to the knob portion.

7. The surgical instrument of claim 1, wherein the wrench body is positioned on the shaft assembly.

8. The surgical instrument of claim 1, wherein the integral torque wrench extends along the longitudinal axis and is configured to rotate about the longitudinal axis.

9. The surgical instrument of claim 1, further comprising:

(a) an instrument body; and (b) an ultrasonic transducer assembly rotatably mounted within the instrument body such that the ultrasonic transducer assembly is configured to selectively rotate about the longitudinal axis, wherein the ultrasonic transducer assembly is configured to rotatably couple with the acoustic waveguide.

10. A surgical instrument, comprising:

(a) an end effector;

(b) a shaft assembly extending proximally from the end effector along a longitudinal axis, wherein the shaft assembly includes:

(i) an acoustic waveguide extending along the longitudinal axis;

(ii) a knob operatively connected to the acoustic waveguide, wherein the knob is configured to be selectively rotated and thereby rotate the acoustic waveguide; and (c) an integral torque wrench, including:

(i) a wrench body, and (ii) a releasable coupling having a body portion positioned on the wrench body and knob portion positioned on the knob, wherein the releasably coupling connects the wrench body to the knob such that the wrench body is configured to rotate with the knob and transmit torque from the wrench body to the knob up to a predetermined torque, wherein the releasable coupling is configured to rotatably release the knob from the wrench body as the transmitted torque exceeds the predetermined torque such that the wrench body rotatably slips relative to the knob for inhibiting the transmission of torque therethrough, wherein the releasable coupling includes a compressible member and a cam, wherein the compressible member is engaged with the cam to transmit torque therethrough, wherein the cam is configured to compress the compressible member as the torque being transmitted therethrough is increased, and wherein the compressible member is configured to slip from the cam to disengage the compressible member from the cam as the torque being transmitted therethrough exceeds the predetermined torque.

11. The surgical instrument of claim 10, wherein at least a portion of the knob portion of the releasable coupling is positioned within the knob.

12. The surgical instrument of claim 10, wherein the body portion of the releasable coupling is configured to deflect relative to the knob portion of the releasable coupling as the transmitted torque exceeds the predetermined torque such that the body portion rotatably slips relative to the knob portion for inhibiting the transmission of torque through the releasable coupling.

13. The surgical instrument of claim 12, wherein the body portion of the releasable coupling is configured to proximally deflect or distally deflect relative to the knob portion.

14. The surgical instrument of claim 12, wherein the body portion of the releasable coupling is configured to resiliently deflect relative to the knob portion.

15. A method of connecting an acoustic waveguide of a surgical instrument to an ultrasonic transducer assembly, the surgical instrument including (a) an end effector; (b) a shaft assembly extending proximally from the end effector along a longitudinal axis, wherein the shaft assembly includes: (i) the acoustic waveguide extending along the longitudinal axis; (ii) a knob operatively connected to the acoustic waveguide, wherein the knob is configured to be selectively rotated and thereby rotate the acoustic waveguide; and (c) an integral torque wrench, including: (i) a wrench body, and (ii) a releasable coupling operatively connecting the wrench body to the knob, the method comprising:

(a) rotating the wrench body with the knob to transmit torque from the wrench body to the knob up to a predetermined torque;

(b) connecting the acoustic waveguide to the ultrasonic transducer assembly as the torque reaches the predetermined torque;

(c) compressing a compressible member of the releasable coupling against a cam of the releasable coupling as the torque being transmitted therethrough is increased thereby slipping the compressible member from the cam; and (d) rotatably slipping the wrench body relative to the knob as the transmitted torque exceeds the predetermined torque thereby inhibiting the transmission of torque therethrough from exceeding the predetermined torque.

16. The method of claim 15, wherein the releasable coupling includes a body portion positioned on the wrench body and a knob portion positioned on the knob, the method further comprising deflecting the body portion of the releasable coupling relative to the knob portion of the releasable coupling as the transmitted torque exceeds the predetermined torque.

17. The method of claim 15, wherein rotating the wrench body with the knob further includes rotating the wrench body about a portion of the shaft assembly with the knob.

18. The method of claim 15, wherein the wrench body is positioned between the knob and the end effector.

* * * * *